(12) United States Patent
Lorian et al.

(10) Patent No.: US 12,161,348 B2
(45) Date of Patent: Dec. 10, 2024

(54) ELECTRICAL DRILL BITS

(71) Applicants: CONFIDENT ABC LTD., Afula (IL); SPINEGUARD S.A., Vincennes (FR)

(72) Inventors: Adi Lorian, Tiberias (IL); Noa Barer, Hod Hasharon (IL); Roy Zilberman, Qaaddarim (IL); Ofer Paz, Tel Aviv (IL); Anbarasan Duraisamy, Singapore (SG); Ulrich Schraudolph, Singapore (SG); Olivier Frezal, Biarritz (FR)

(73) Assignees: CONFIDENT ABC LTD., Afula (IL); SPINEGUARD S.A., Vincennes (FR)

( * ) Notice: Subject to any disclaimer, the term of this patent is extended or adjusted under 35 U.S.C. 154(b) by 380 days.

(21) Appl. No.: 17/781,578

(22) PCT Filed: Dec. 2, 2020

(86) PCT No.: PCT/IL2020/051241
§ 371 (c)(1),
(2) Date: Jun. 1, 2022

(87) PCT Pub. No.: WO2021/111439
PCT Pub. Date: Jun. 10, 2021

(65) Prior Publication Data
US 2022/0409214 A1    Dec. 29, 2022

Related U.S. Application Data

(60) Provisional application No. 62/942,520, filed on Dec. 2, 2019.

(51) Int. Cl.
*A61B 17/16* (2006.01)
*A61B 17/00* (2006.01)
(Continued)

(52) U.S. Cl.
CPC ........ *A61B 17/1615* (2013.01); *A61B 17/162* (2013.01); *A61B 17/1622* (2013.01);
(Continued)

(58) Field of Classification Search
CPC .............. A61B 17/1615; A61B 17/162; A61B 17/1626; A61B 17/1622; A61B 17/1617;
(Continued)

(56) References Cited

U.S. PATENT DOCUMENTS 6,337,994 B1 * 1/2002 Stoianovici .......... A61B 5/0538
600/373
7,580,743 B2 8/2009 Bourlion et al.
(Continued)

*Primary Examiner* — Marcela I. Shirsat
(74) *Attorney, Agent, or Firm* — Maschoff Brennan

(57) ABSTRACT

A drill bit is provided that includes a connector, which includes a shank, configured to receive torque; a proximal electrically-conductive coupler, which is disposed at a distal end of the shank, rotationally fixed with respect to the shank; and a distal electrically-conductive coupler. The distal electrically-conductive coupler is rotationally fixed with respect to the proximal electrically-conductive coupler, electrically isolated from the proximal electrically-conductive coupler, and shaped so as to define a distal-electrically-conductive external contact surface. The drill bit further includes a drill shaft including an electrically-conductive outer electrode and an electrically-conductive inner electrode. Other embodiments are also described.

19 Claims, 27 Drawing Sheets

(51) Int. Cl.
*A61B 17/34* (2006.01)
*A61B 18/00* (2006.01)
*A61B 18/14* (2006.01)
*A61F 2/30* (2006.01)
*A61N 1/04* (2006.01)
*A61N 1/05* (2006.01)

(52) U.S. Cl.
CPC .............. *A61B 2017/00017* (2013.01); *A61B 2017/00026* (2013.01); *A61B 2017/00097* (2013.01); *A61B 2017/00477* (2013.01); *A61B 17/1624* (2013.01); *A61B 17/1662* (2013.01); *A61B 17/3476* (2013.01); *A61B 2018/00071* (2013.01); *A61B 2018/1412* (2013.01); *A61B 2018/1467* (2013.01); *A61B 2018/1497* (2013.01); *A61B 2560/0468* (2013.01); *A61B 2562/182* (2013.01); *A61F 2002/30087* (2013.01); *A61F 2002/30668* (2013.01); *A61N 1/04* (2013.01); *A61N 1/048* (2013.01); *A61N 1/0502* (2013.01)

(58) Field of Classification Search
CPC ............ A61B 17/1624; A61B 17/1628; A61B 17/1631; A61B 17/1633; A61B 17/1655; A61B 17/1657; A61B 17/1662; A61B 17/7016; A61B 17/3476; A61B 2017/00026; A61B 2017/00477; A61B 2017/00017; A61B 2017/00039; A61B 2017/0011; A61B 2017/00929; A61B 2017/00097; A61B 2018/00071; A61B 2018/00178; A61B 2018/1405; A61B 2018/1412; A61B 2018/1415; A61B 2018/1467; A61B 2018/147; A61B 2018/1497; A61B 18/14; A61B 18/00; A61B 18/00178; A61B 18/08; A61B 18/082; A61B 18/1402; A61B 2090/08021; A61B 5/15115; A61B 5/15121; A61B 5/301; A61B 2562/18; A61B 2562/182; A61C 5/42; A61C 3/02; A61C 3/00; A61F 2002/30087; A61F 2002/30668; A61F 2560/0468; A61N 1/048; A61N 1/04; A61N 1/0502
USPC ....... 606/80, 53, 60, 76, 79, 167–189, 86 R, 606/129; 128/908
See application file for complete search history.

(56) References Cited

U.S. PATENT DOCUMENTS

| | | | |
|---|---|---|---|
| 8,326,414 B2 * | 12/2012 | Neubardt | A61B 17/1626 607/116 |
| 10,064,630 B2 | 9/2018 | Forman et al. | |
| 2006/0241628 A1 | 10/2006 | Parak | |
| 2007/0218420 A1 * | 9/2007 | Syribeys | A61C 5/42 433/32 |
| 2008/0086140 A1 * | 4/2008 | Wolf | A61B 5/05 606/39 |
| 2008/0262526 A1 | 10/2008 | Neubardt et al. | |
| 2013/0296734 A1 | 11/2013 | Bourlion et al. | |
| 2014/0276839 A1 * | 9/2014 | Forman | A61B 17/1622 173/2 |
| 2020/0324408 A1 * | 10/2020 | Bourlion | A61B 34/30 |

\* cited by examiner

ELECTRICAL DRILL BITS

CROSS-REFERENCE TO RELATED APPLICATIONS

The present patent application claims priority from U.S. Provisional Application 62/942,520, filed Dec. 2, 2019, which is incorporated herein by reference.

FIELD OF THE APPLICATION

The present invention relates generally to drill bits, and specifically to electrical drill bits.

BACKGROUND OF THE APPLICATION

Some surgical procedures, including dental and orthopedic procedures, include drilling through tissue that includes both bone and soft tissue. It is important for the surgeon to know at all times whether the tip of the drill bit remains in bone or has come out of the bone and penetrated soft tissue.

U.S. Pat. No. 7,580,743 to Bourlion et al. describes a device that can be used to monitor the penetration of a penetration member into anatomical structures and, in particular, bone structures of a living body, the structures having at least two different electrical impedance areas. The device is characterized in that it comprises at least one impedance meter which can be connected to at least two electrodes, at least one of the electrodes being located at a distal end of the penetration member, and at least one alert device which can produce an alert signal if the impedance meter detects an impedance variation. The '743 patent also describes a penetration member for the device and to an electronic board for the device.

U.S. Pat. No. 10,064,630 to Forman et al. describes driver assemblies, drivers, drill bits, and methods for determining information (such as impedances, voltages, voltage differences, and changes in such information) about biological material during a medical procedure

SUMMARY OF THE APPLICATION

Some embodiments of the present invention provide a drill bit that comprises a connector and a drill shaft. The connector comprises a shank, a proximal electrically-conductive coupler, a distal electrically-conductive coupler, and an insulator that electrically isolates the distal electrically-conductive coupler from the proximal electrically-conductive coupler. The shank is configured to receive torque, typically from a chuck of a surgical drill, such as a dental handpiece. The proximal electrically-conductive coupler is disposed at a distal end of the shank, rotationally fixed with respect to the shank. The distal electrically-conductive coupler is rotationally fixed with respect to the proximal electrically-conductive coupler, electrically isolated from the proximal electrically-conductive coupler, and shaped so as to define a distal-electrically-conductive external contact surface.

The drill shaft is shaped so as to define a proximal interface that is rotationally fixed with respect to the proximal electrically-conductive coupler and configured to transfer the torque from the proximal electrically-conductive coupler to the drill shaft. The drill shaft is shaped so as to further define a distal end portion that is shaped so as to penetrate tissue.

The drill shaft comprises:
- an electrically-conductive outer electrode, which is in electrical communication with the distal electrically-conductive coupler;
- an electrically-conductive inner electrode, which has a proximal end portion that is in electrical communication with the proximal electrically-conductive coupler of the connector, and is electrically isolated from the distal electrically-conductive coupler of the connector; and
- an electrical isolation layer radially between the electrically-conductive outer electrode and the electrically-conductive inner electrode, so as to electrically isolate the electrically-conductive outer electrode and the electrically-conductive inner electrode from each other.

The drill shaft and the connector are configured to transfer the torque from a surgical drill to the drill shaft so as to penetrate tissue. The drill shaft and the connector are configured to provide an electrical connection between the electrically-conductive outer and inner electrodes and a central unit that is configured sense electrical properties of the tissue penetrated by the drill shaft, such as impedance, change in impedance, voltage, or change in voltage. The sensed electrical properties may be used by the operator of a surgical drill to which the drill bit is coupled in order to monitor the penetration of the drill shaft into anatomical structures and, in particular, bone structures having at least two different electrical impedance areas, such as bone (e.g., cortical bone) and soft tissue. In addition, the sensed electrical properties enable the measurement of local electrical properties of the tissue, which are more difficult, if not impossible, to measure using a single electrode on the drill bit and a remote external skin return electrode, as is known in the impedance measurement drill art.

There is therefore provided, in accordance with an application of the present invention, a drill bit including:
(a) a connector, which includes:
 (i) a shank, configured to receive torque;
 (ii) a proximal electrically-conductive coupler, which is disposed at a distal end of the shank, rotationally fixed with respect to the shank; and
 (iii) a distal electrically-conductive coupler, which is (1) rotationally fixed with respect to the proximal electrically-conductive coupler, (2) electrically isolated from the proximal electrically-conductive coupler, and (3) shaped so as to define a distal-electrically-conductive external contact surface; and
(b) a drill shaft, which is shaped so as to define:
 (i) a proximal interface that is rotationally fixed with respect to the proximal electrically-conductive coupler and configured to transfer the torque from the proximal electrically-conductive coupler to the drill shaft, and
 (ii) a distal end portion that is shaped so as to penetrate tissue when rotated,
wherein the drill shaft includes:
 (i) an electrically-conductive outer electrode, which is in electrical communication with the distal electrically-conductive coupler;
 (ii) an electrically-conductive inner electrode, which has a proximal end portion that is in electrical communication with the proximal electrically-conductive coupler of the connector, and is electrically isolated from the distal electrically-conductive coupler of the connector; and
 (iii) an electrical isolation layer radially between the electrically-conductive outer electrode and the electrically-conductive inner electrode, so as to electrically isolate the electrically-conductive outer electrode and the electrically-conductive inner electrode from each other.

For some applications, the shank is shaped so as to define a non-cross-sectionally-circular proximal axial portion for receiving the torque.

For some applications, the shank is shaped so as to define a cross-sectionally-circular proximal axial portion for receiving the torque.

For some applications, the proximal interface of the drill shaft is rotationally fixed to the proximal electrically-conductive coupler via the distal electrically-conductive coupler.

For some applications, the distal electrically-conductive coupler is integral to the drill shaft at the proximal interface of the drill shaft.

For some applications, the distal electrically-conductive coupler and the drill shaft include separate pieces that are coupled together at the proximal interface of the drill shaft.

For some applications, the connector and the drill shaft include separate pieces that are removably couplable to each other.

For some applications, the proximal end portion of the electrically-conductive inner electrode and the proximal electrically-conductive coupler of the connector include separate pieces that are directly coupled to each other.

For some applications, the proximal end portion of the electrically-conductive inner electrode is integral with the proximal electrically-conductive coupler of the connector.

For some applications:
the connector further includes an internal electrical contact, which is in electrical contact with the proximal electrically-conductive coupler and is electrically isolated from the distal electrically-conductive coupler, and
the proximal end portion of the electrically-conductive inner electrode is in electrical communication with the proximal electrically-conductive coupler via the internal electrical contact.

For some applications, the internal electrical contact includes a contact spring.

For some applications, the contact spring is in axial contact with the proximal end portion of the electrically-conductive inner electrode.

For some applications, the contact spring is in lateral contact with the proximal end portion of the electrically-conductive inner electrode.

For some applications, the electrically-conductive inner electrode protrudes proximally from the distal electrically-conductive coupler of the connector.

For some applications, the electrically-conductive inner electrode is recessed within the distal electrically-conductive coupler of the connector.

For some applications, the electrically-conductive inner electrode is flush with the distal electrically-conductive coupler of the connector.

For some applications, a length of the shank, measured between a proximal end of the shank and the distal end of the shank, is between 5 and 30 mm.

For some applications, a length of the shank, measured between a proximal end of the shank and the distal end of the shank, is between 5 and 30 mm.

For some applications, a length of the drill shaft, measured between the proximal interface of the drill shaft and a distal tip of the drill shaft, is between 3 and 80 mm.

For some applications, the electrically-conductive inner electrode is flush with a proximal end of the drill shaft.

For some applications, the electrically-conductive inner electrode is recessed within a proximal end of the drill shaft.

For some applications, the electrically-conductive inner electrode protrudes proximally from a proximal end of the drill shaft.

For some applications, a length of the drill shaft, measured between the proximal interface of the drill shaft and a distal tip of the drill shaft, equals between 25% and 95% of a length of the drill bit, measured between the proximal end of the shank and a distal tip of the drill shaft.

For some applications, the connector includes an insulator that electrically isolates the distal electrically-conductive coupler from the proximal electrically-conductive coupler.

For some applications, the distal electrically-conductive coupler is rotationally fixed to the proximal electrically-conductive coupler via the insulator.

For some applications, the distal electrically-conductive coupler is rotationally fixed to the proximal electrically-conductive coupler via the insulator via a lateral mechanical connection.

For some applications, the distal electrically-conductive coupler is rotationally fixed to the proximal electrically-conductive coupler via the insulator via an axial mechanical connection.

For some applications, the insulator includes an isolation ring, which is configured to electrically isolate the distal electrically-conductive coupler and the proximal electrically-conductive coupler from each other.

For some applications, the insulator includes a coating.

For some applications, the insulator includes non-conductive glue.

For some applications, the connector includes a non-conductive spacer that electrically isolates the distal electrically-conductive coupler from the proximal electrically-conductive coupler.

For some applications, the non-conductive spacer electrically isolates the distal electrically-conductive coupler from the proximal electrically-conductive coupler in part by defining one or more empty gaps between the distal electrically-conductive coupler and the proximal electrically-conductive coupler.

For some applications, the distal-electrically-conductive external contact surface surrounds 360 degrees of a central longitudinal axis of the connector.

For some applications, the distal-electrically-conductive external contact surface faces at least partially radially outward.

For some applications, the distal-electrically-conductive external contact surface has a circular external cross-section.

For some applications, the distal-electrically-conductive external contact surface faces at least partially distally.

For some applications, the proximal electrically-conductive coupler is disposed at least partially proximal to the distal electrically-conductive external contact surface For some applications, the proximal electrically-conductive coupler is shaped so as to define a proximal-electrically-conductive external contact surface.

For some applications, the proximal electrically-conductive external contact surface surrounds 360 degrees of a central longitudinal axis of the connector.

For some applications, the proximal-electrically-conductive external contact surface faces at least partially radially outward.

For some applications, the proximal electrically-conductive external contact surface has a circular external cross-section.

For some applications, the proximal-electrically-conductive external contact surface faces at least partially proximally.

For some applications, the drill system is for use with a surgical drill, and the drill system further includes a contact holder, which (a) is configured to be mechanically coupled to the surgical drill, and (b) includes:

proximal and distal electrical connectors, the contact holder is configured to bring the proximal and the distal electrical connectors in electrical contact with the proximal-electrically-conductive external contact surface and the distal-electrically-conductive external contact surface, respectively, when the connector is received by the contact holder.

For some applications, the distal electrical connector includes a blade, the proximal electrical connector includes a blade, or the distal and the proximal electrical connector include respective blades.

For some applications, the distal electrical connector includes a brush, the distal electrical connector includes a brush, or the distal and the proximal electrical connectors include respective brushes.

For some applications, the distal electrical connector includes a rigid contact, the distal electrical connector includes a rigid contact, or the distal and the proximal electrical connectors include respective rigid contacts.

For some applications:

the proximal electrically-conductive coupler is shaped so as to define a proximal-electrically-conductive external contact surface that faces at least partially proximally, and the contact holder is configured to bring the proximal electrical connector in electrical contact with the proximal-electrically-conductive external contact surface, when the connector is received by the contact holder.

For some applications, the proximal-electrically-conductive external contact surface faces entirely proximally.

For some applications, the proximal electrical connector includes a blade.

For some applications:

the distal-electrically-conductive external contact surface faces at least partially distally, and the contact holder is configured to bring the distal electrical connector in electrical contact with the distal-electrically-conductive external contact surface, when the connector is received by the contact holder.

For some applications, the distal-electrically-conductive external contact surface faces entirely distally.

For some applications, the distal electrical connector includes a blade.

For some applications, the contact holder includes a clamp, which is configured to mechanically couple the contact holder to the surgical drill.

For some applications, the contact holder is shaped so as to define a channel for receiving the connector.

For some applications, the drill system further includes the surgical drill.

For some applications, the proximal electrically-conductive coupler is in electrical communication with the shank.

For some applications, the drill bit is for use with a surgical drill, and the shank of the connector is configured to be electrically connected to the surgical drill.

For some applications, the drill system further includes the surgical drill.

For some applications, the drill system is for use with a surgical drill, and the drill system further includes a contact holder, which (a) is configured to be mechanically coupled to the surgical drill, and (b) includes:

a distal electrical connector, wherein the contact holder is configured to bring the distal electrical connector in electrical contact with the distal-electrically-conductive external contact surface when the connector is received by the contact holder; and a surgical drill electrical connector, which is configured to be electrically coupled to the surgical drill.

For some applications, the distal electrical connector includes a blade.

For some applications, the distal electrical connector includes a brush.

For some applications, the distal electrical connector includes a rigid contact.

For some applications:

the distal-electrically-conductive external contact surface faces at least partially distally, and the contact holder is configured to bring the distal electrical connector in electrical contact with the distal-electrically-conductive external contact surface, when the connector is received by the contact holder.

For some applications, the distal-electrically-conductive external contact surface faces entirely distally.

For some applications, the distal electrical connector includes a blade.

For some applications, the contact holder includes a clamp, which is configured to mechanically couple the contact holder to the surgical drill.

For some applications, the drill system further includes the surgical drill.

For some applications, the contact holder is shaped so as to define a channel for receiving the connector.

For some applications, the drill system is for use with a surgical drill, and the drill system further includes a contact holder, which (a) is configured to be mechanically coupled to the surgical drill, and (b) includes:

proximal and distal electrical connectors, and the contact holder is configured to bring the proximal and the distal electrical connectors in electrical contact with the shank and the distal-electrically-conductive external contact surface, respectively, when the connector is received by the contact holder.

For some applications:

the distal-electrically-conductive external contact surface faces at least partially distally, and the contact holder is configured to bring the distal electrical connector in electrical contact with the distal-electrically-conductive external contact surface, when the connector is received by the contact holder.

For some applications, the distal-electrically-conductive external contact surface faces entirely distally.

For some applications, the distal electrical connector includes a blade.

For some applications, the drill system for use with a surgical drill, the drill system further includes a contact holder, which (a) is configured to be mechanically coupled to the surgical drill, and (b) includes a distal electrical connector, and the contact holder is configured to bring the distal electrical connector in electrical contact with the distal-electrically-conductive external contact surface when the connector is received by the contact holder.

For some applications:

the distal-electrically-conductive external contact surface faces at least partially distally, and the contact holder is configured to bring the distal electrical connector in electrical contact with the distal-electrically-conductive external contact surface, when the connector is received by the contact holder.

For some applications, the distal-electrically-conductive external contact surface faces entirely distally.

For some applications, the distal electrical connector includes a blade.

For some applications, the drill system further includes a surgical drill, which includes a chuck, and the shank is configured to be coupled to the chuck, so as to receive the torque from the chuck.

There is further provided, in accordance with an application of the present invention, a method of using the drill bit of any the applications described above, the method including:

coupling the shank to a chuck of a surgical drill;

coupling the proximal and distal electrically-conductive couplers in electrical communication with a central unit;

activating the surgical drill to penetrate the distal end portion of the drill shaft into tissue; and using the central unit, measuring an electrical characteristic of the tissue sensed via the electrically-conductive outer and inner electrodes.

The present invention will be more fully understood from the following detailed description of embodiments thereof, taken together with the drawings, in which:

DETAILED DESCRIPTION OF EMBODIMENTS

Figure 1A:
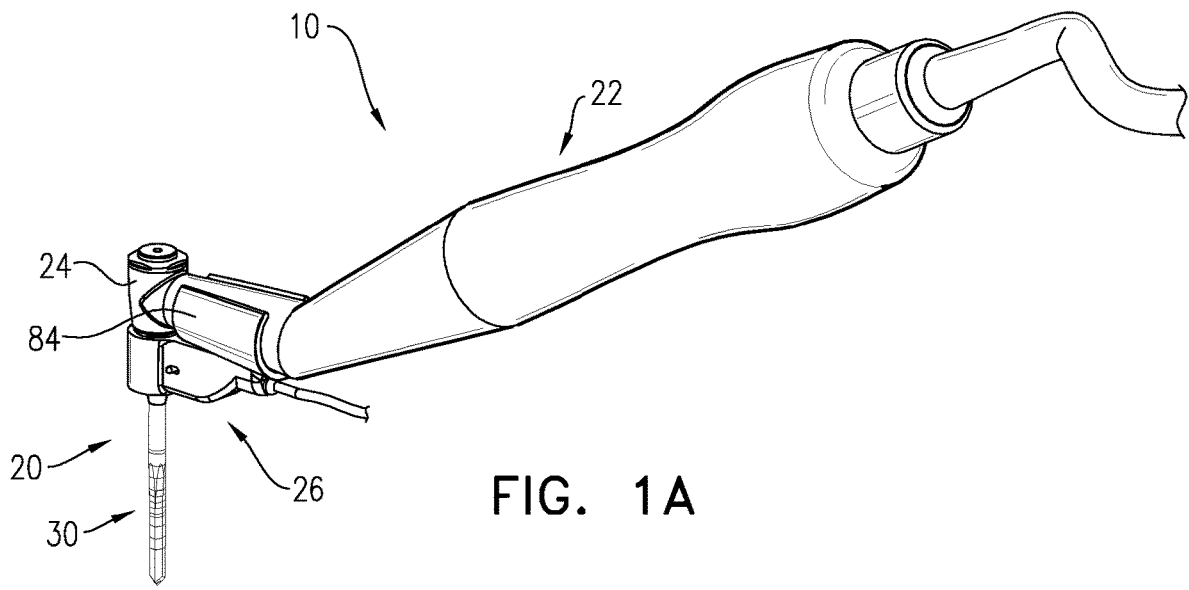
FIGS. 1A-B are schematic illustrations of a drill system, in accordance with an application of the present invention.
Figure 1B:
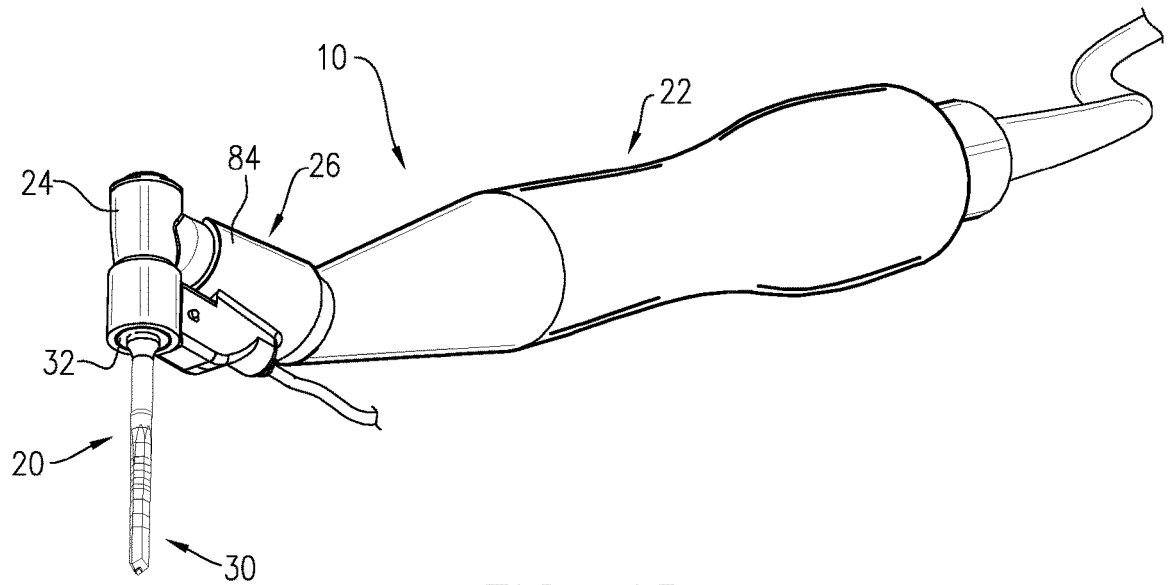

FIGS. 1A-B are schematic illustrations of a drill system 10, in accordance with an application of the present invention. Drill system 10 comprises a drill bit 20 and a surgical drill 22, such as a dental handpiece (as shown) or another type of surgical drill, e.g., an orthopedic surgical drill (not shown). FIGS. 1A-B show drill bit 20 secured to a chuck 24 of surgical drill 22. For some applications, surgical drill 22 is conventional, such as those commercially available. Optionally, chuck 24 comprises a collet, as known in the drill art, while for other applications, the chuck does not comprise a collet, as is also known in the drill art.

Figure 2A:
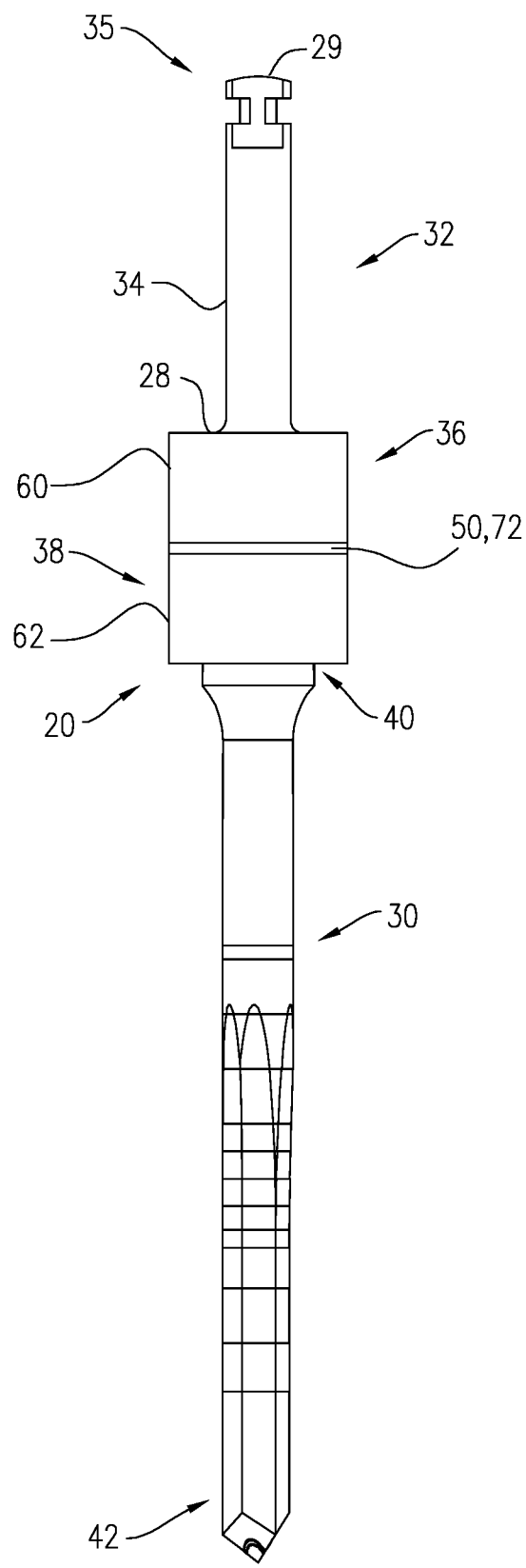
FIGS. 2A-B are schematic illustrations of a drill bit of the drill system of FIGS. 1A-B, in accordance with an application of the present invention.
Figure 2B:
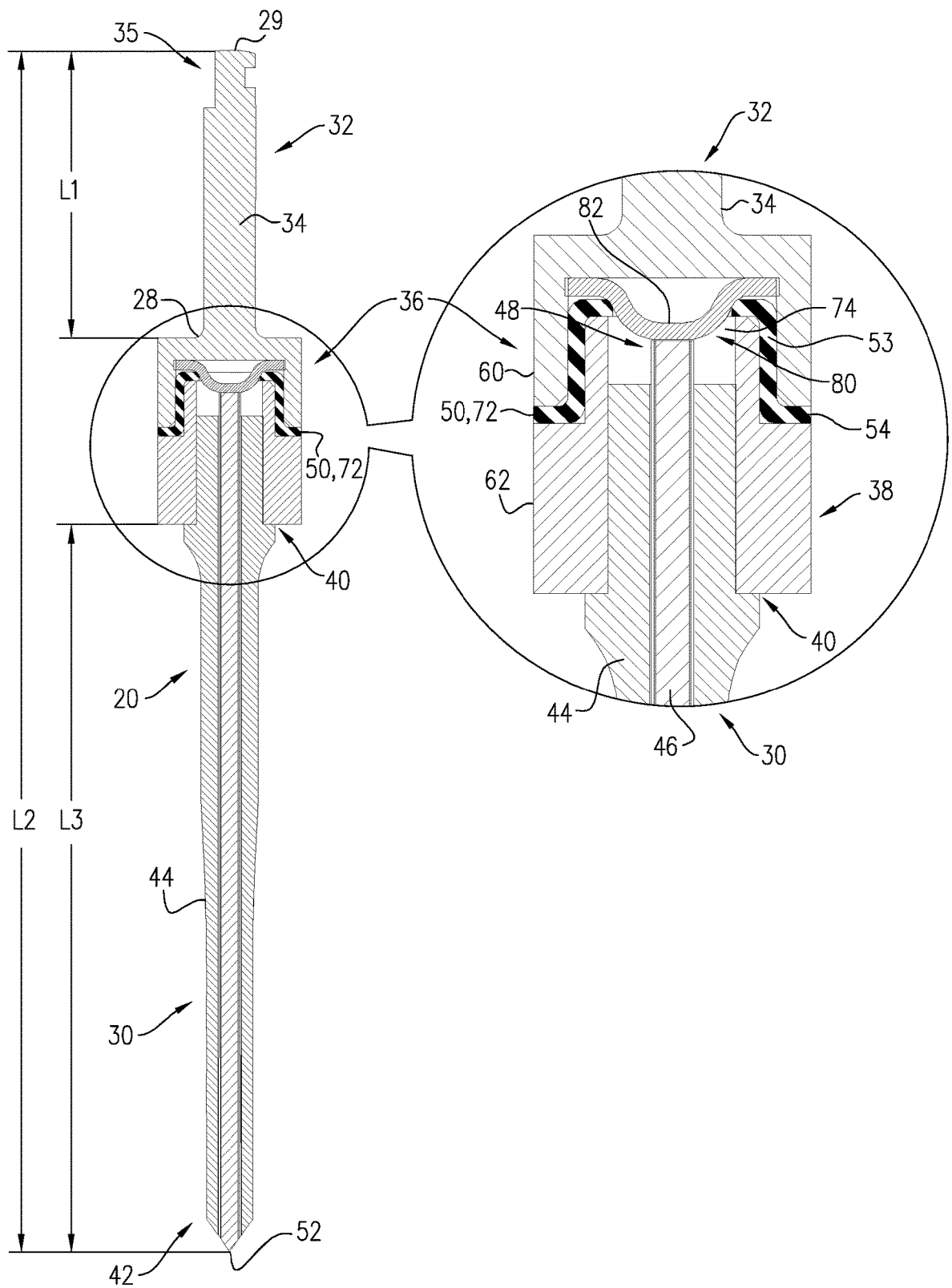

Reference is additionally made to FIGS. 2A-B, which are schematic illustrations of drill bit 20, in accordance with an application of the present invention.

Figure 3A:
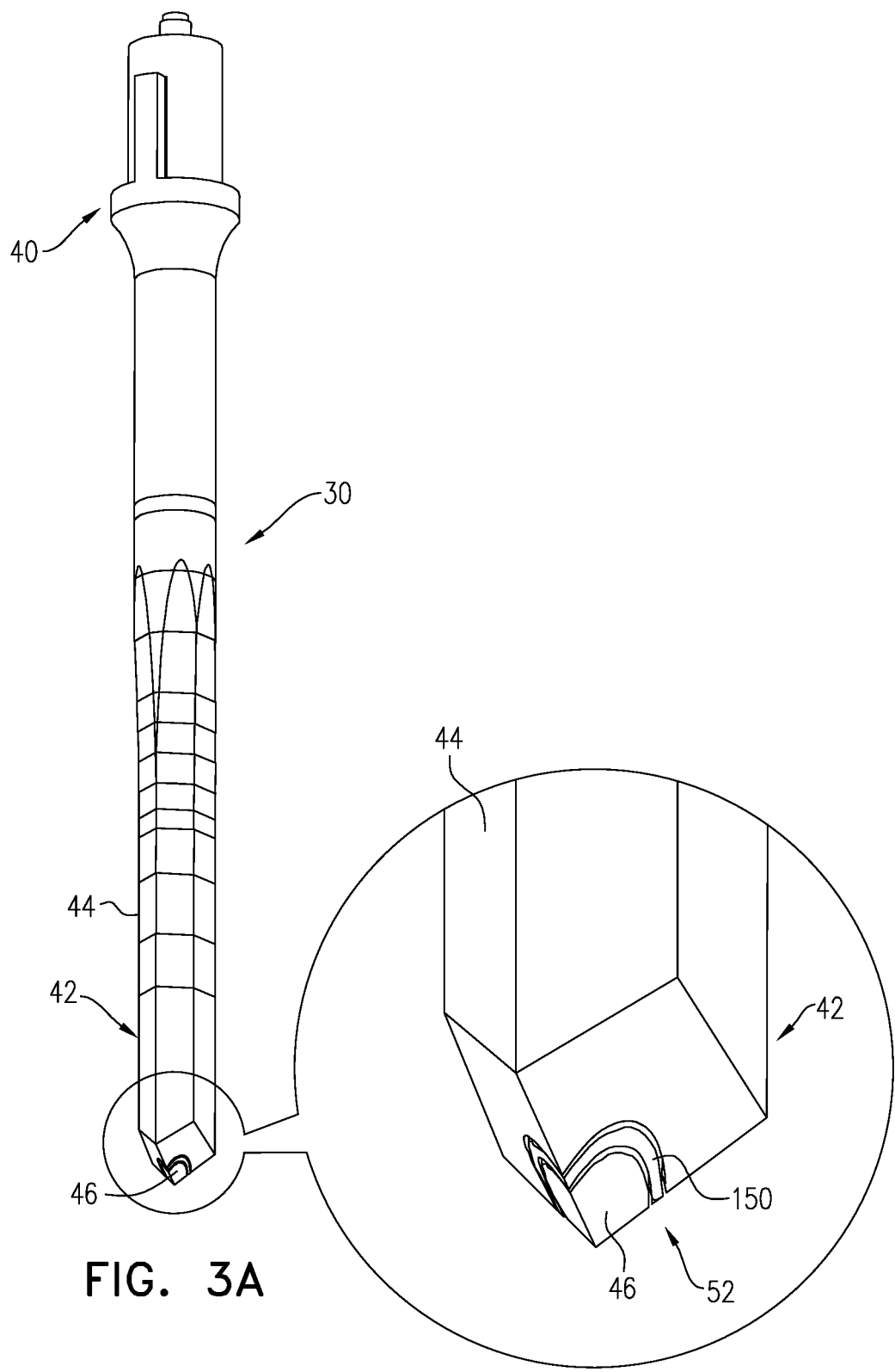
FIGS. 3A-C are schematic illustrations of a drill shaft of the drill bit of FIGS. 2A-B, in accordance with an application of the present invention.
Figure 3B:
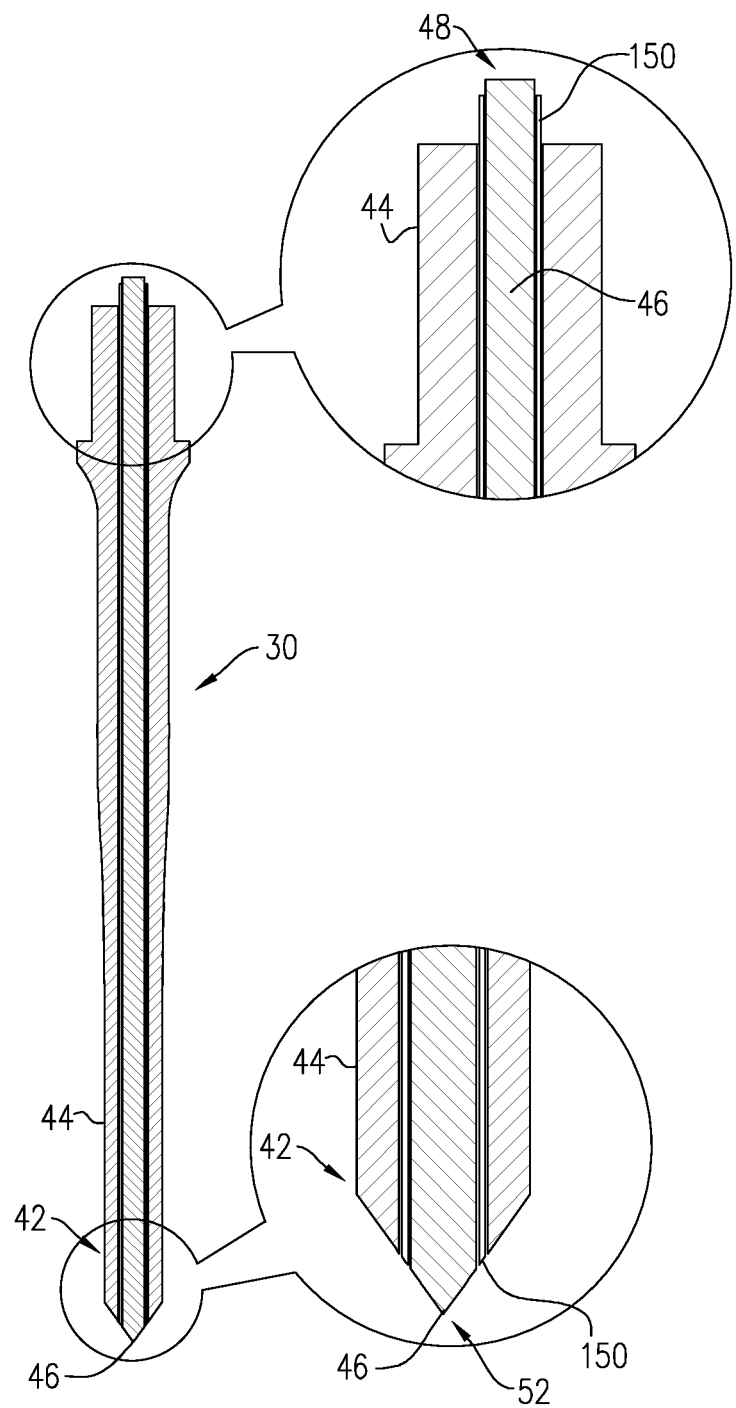
Figure 3C:
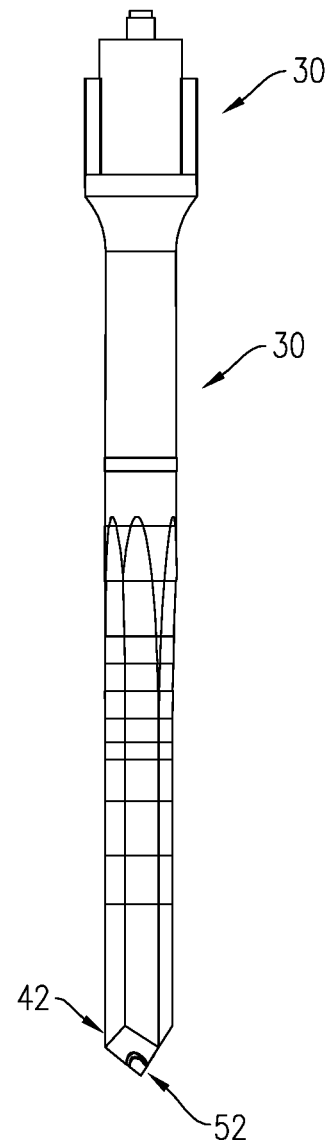

Reference is yet additionally made to FIGS. 3A-C, which are schematic illustrations of a drill shaft 30 of drill bit 20, in accordance with an application of the present invention.

Figure 4A:
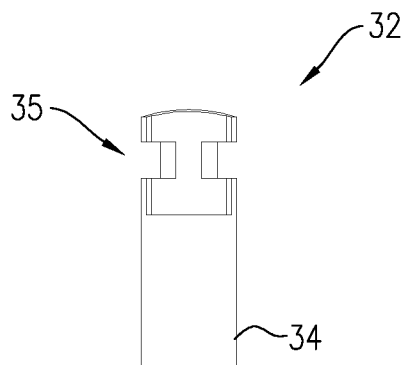
FIGS. 4A-B are schematic illustrations of a connector of the drill bit of FIGS. 2A-B, in accordance with an application of the present invention.
Figure 4A:
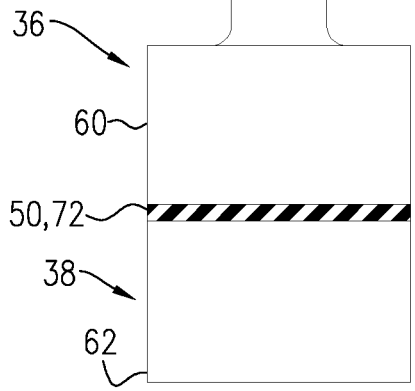
Figure 4B:
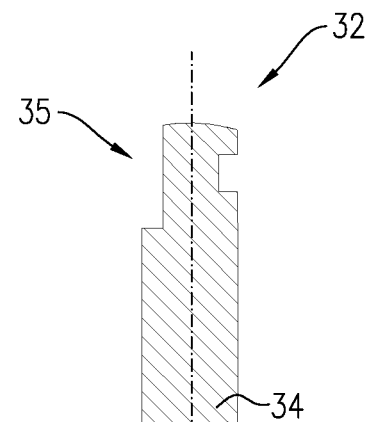
Figure 4B:
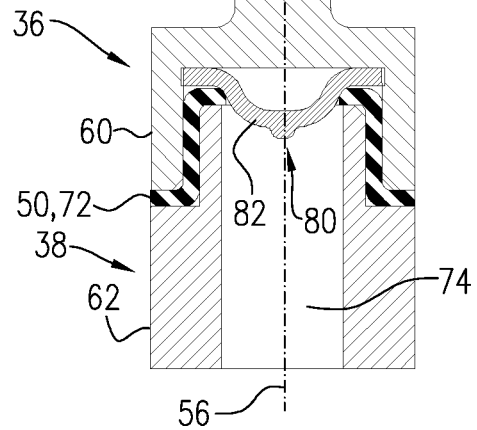

Reference is also made to FIGS. 4A-B, which are schematic illustrations of a connector 32 of drill bit 20, in accordance with an application of the present invention.

For some applications, connector 32 of drill bit 20 comprises:
- a shank 34, configured to receive torque, typically from chuck 24 of surgical drill 22;
- a proximal electrically-conductive coupler 36, which is disposed at a distal end 28 of shank 34, rotationally fixed with respect to shank 34; and
- a distal electrically-conductive coupler 38, which is rotationally fixed with respect to proximal electrically-conductive coupler 36, electrically isolated from proximal electrically-conductive coupler 36.

Connector 32 is configured to transfer rotational motion and torque from surgical drill 22 to drill bit 20, and to electrically connect drill bit 20 to a contact holder 26 mechanically couplable to surgical drill 22, such as described hereinbelow in detail, in order to enable transmission of an electrical signal between drill bit 20 and a central unit 21, described hereinbelow with reference to FIG. 11.

Figure 20A:
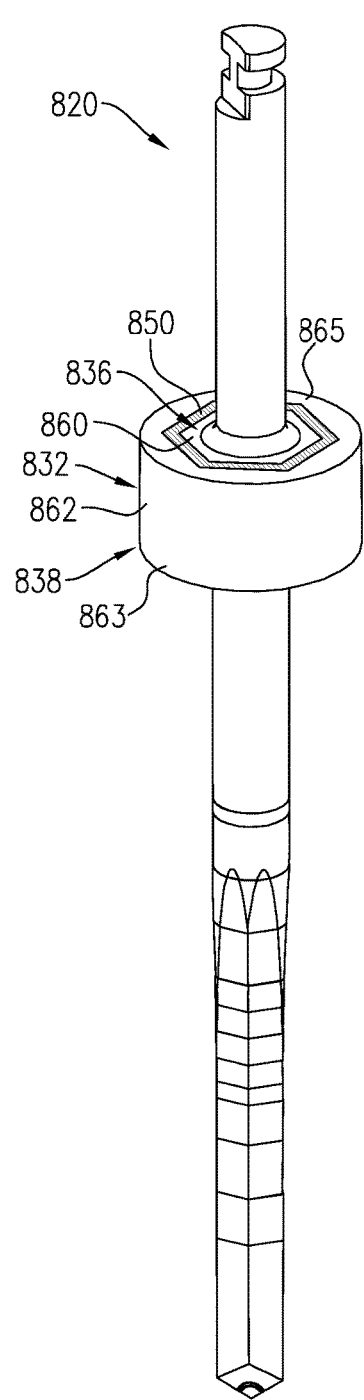
FIGS. 20A-B and 20C are schematic illustrations of respective configurations of another drill bit, in accordance with respective applications of the present invention.
Figure 20B:
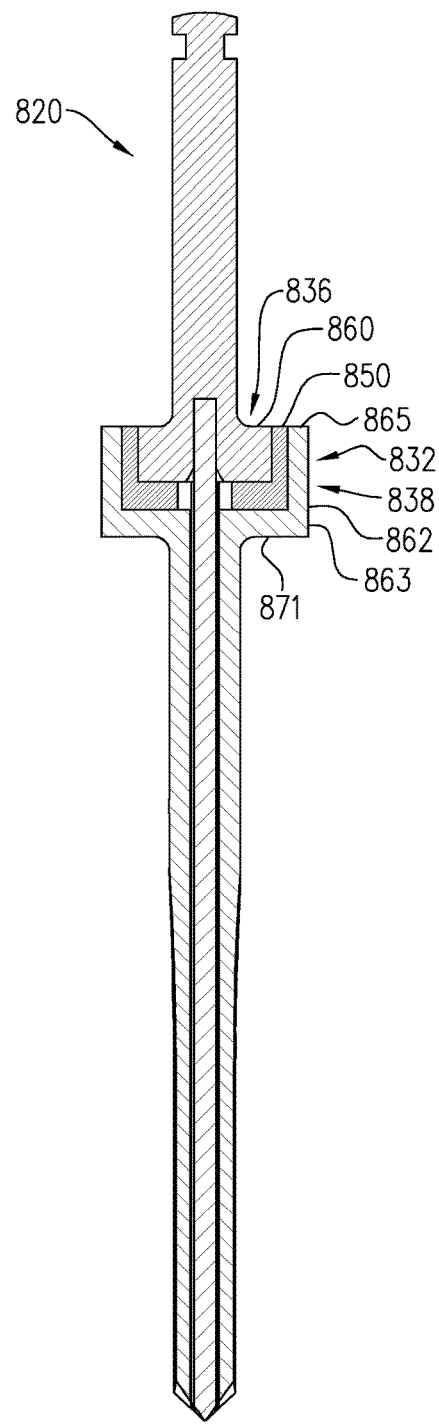
Figure 20C:
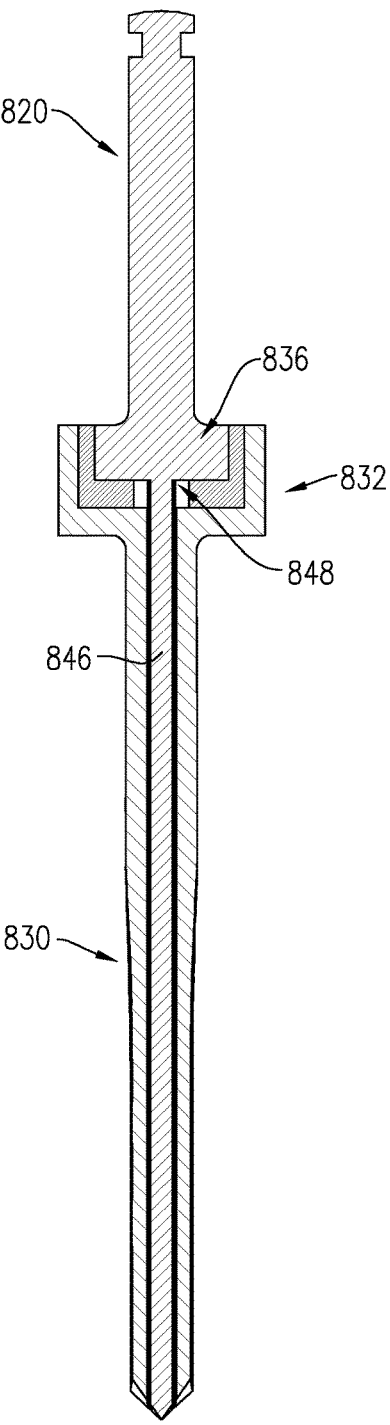

Typically, distal electrically-conductive coupler 38 is shaped so as to define a distal-electrically-conductive external contact surface 62. For some applications, proximal electrically-conductive coupler 36 is disposed at least partially proximal to distal-electrically-conductive external contact surface 62, such as entirely proximal to distal-electrically-conductive external contact surface 62. For other applications, proximal electrically-conductive coupler 36 is not disposed at least partially proximal to distal-electrically-conductive external contact surface 62, such as shown in FIGS. 20A-C; for example, proximal electrically-conductive coupler 36 may be disposed at the same axial location as at least a portion of distal-electrically-conductive external contact surface 62.

For some applications, drill shaft 30 is shaped so as to define:
- a proximal interface 40 that is rotationally fixed with respect to proximal electrically-conductive coupler 36 and configured to transfer the torque from proximal electrically-conductive coupler 36 to drill shaft 30, and
- a distal end portion 42 that is shaped so as to penetrate tissue, e.g., when rotated (such as by cutting and/or grinding) or oscillated; the tissue may include bone (e.g., cortical bone) and/or soft tissue.

For some applications, drill shaft 30 comprises:
- an electrically-conductive outer electrode 44, which is in electrical communication with distal electrically-conductive coupler 38;
- an electrically-conductive inner electrode 46, which has a proximal end portion 48 that is in electrical communication with proximal electrically-conductive coupler 36 of connector 32, and is electrically isolated from distal electrically-conductive coupler 38 of connector 32; and
- an electrical isolation layer 150 (labeled in FIGS. 3A-B) radially between electrically-conductive outer electrode 44 and electrically-conductive inner electrode 46, so as to electrically isolate electrically-conductive outer electrode 44 and electrically-conductive inner electrode 46 from each other.

For some applications, proximal end portion 48 of electrically-conductive inner electrode 46 is in direct electrical communication with proximal electrically-conductive coupler 36 of connector 32 (configuration not shown). For other applications, proximal end portion 48 of electrically-conductive inner electrode 46 is in indirect electrical communication with proximal electrically-conductive coupler 36 of connector 32, such as via shank 34 (configuration shown in FIG. 17) or another element of drill bit 20, such as a contact spring 82 (configuration shown in FIGS. 2B, 6B, 13A-C, and 15).

For some applications, drill shaft 30 comprises exactly one electrically-conductive inner electrode 46, while for other applications, drill shaft 30 comprises a plurality of electrically-conductive inner electrodes 46, i.e., is multi-polar, such as for applications having drill bits with diameters sufficiently large to accommodate more than two electrodes, for example, some orthopedic drill bits.

Optionally, drill shaft 30 may be marked with depth markings.

Distal end portion 42 of drill shaft 30 is shaped so as to define a distal tip 52. Typically, distal tip 52, and optionally a distal portion of electrically-conductive outer electrode 44, are shaped so as to penetrate the tissue. Optionally, distal tip 52 is sharp. Alternatively, distal tip 52 is not dull. For some applications, electrically-conductive outer electrode 44 is shaped as a trocar (at least 3 surfaces), a drill bit, or a cylinder.

For some applications, such as shown in FIGS. 2A-B, 3A-C, 12A-B, 13A-D, 14A-B, 15, 16, 20A-C, 21A-B, and 22A-B, electrically-conductive inner electrode 46 protrudes from electrically-conductive outer electrode 44 at distal end portion 42 of drill shaft 30, such that electrically-conductive inner electrode 46 is shaped so as to define a distal tip 52 of the drill shaft 30.

Shank 34 is shaped so as to define a proximal axial portion 35 for receiving the torque from chuck 24, either directly or indirectly via an adaptor. Shank 34 may be a universal shank or a custom shank. Proximal axial portion 35 may be non-cross-sectionally-circular or cross-sectionally-circular. For example, cross-sectionally-circular proximal axial portion 35 may have an outer diameter of between 1 and 10 mm for receiving the torque.

For some applications, an outer diameter of shank 34 is between 1.5 and 4 mm, such as between 1.6 and 3 mm, e.g., 2.35 mm.

For some applications, such as shown in the drawings, an outer diameter of shank 34 is:
- less than an outer diameter of connector 32, such as less than 90%, e.g., less than 70%, such as less than 50%, e.g., less than 30%, such as less than 25%, of the outer diameter of connector 32, and/or
- at least 10%, e.g., at least 20%, such as at least 30% of the outer diameter of connector 32 (for example, about 25% of the outer diameter of connector 32).

For other applications, the outer diameter of shank 34 equals the outer diameter of connector 32 (configuration not shown), or is greater than the outer diameter of connector 32 (configuration not shown).

Reference is made to FIG. 2B. For some applications, such as those in which drill bit 20 is a dental drill bit, a length L1 of shank 34, measured between a proximal end 29 of shank 34 and distal end 28 of shank 34:
- is between 5 and 30 mm, such as between 10 and 20 mm, e.g., 15 mm, and/or
- equals at least 5%, e.g., at least 10%, such as at least 15%, e.g., at least 20%, such as at least 25% of a length L2 of drill bit, measured between proximal end 29 of shank 34 and distal tip 52 of drill shaft 30; no more than 95%, such as no more than 70%, e.g., no more than 60%, such as no more than 50%, e.g., no more than 45% of length L2; and/or between 5% and 70%, e.g., between 10% and 60%, such as between 15% and 50%, e.g., between 20% and 45%, such as between 25% and 45%, e.g., 40%, of length L2.

Alternatively or additionally, for some applications, a length L3 of drill shaft 30, measured between proximal interface 40 of drill shaft 30 and distal tip 52 of drill shaft 30:
- is between 3 and 80 mm, such as between 5 and 65 mm, e.g. 13 mm, and/or
- equals at least 25%, such as at least 50% of length L2; no more than 95%, e.g., no more than 90%; and/or between 30% and 95%, such as between 50% and 90%, e.g., 48%, of length L2 of drill bit 20, measured between proximal end of shank 34 and a distal tip 52 of drill shaft 30.

For some applications, such as those in which drill bit 20 is an orthopedic drill bit, a length L1 of shank 34, measured between a proximal end 29 of shank 34 and distal end 28 of shank 34:
- is between 5 mm and 50 mm, such as between 10 and 30 mm, e.g., 20 mm, and/or
- equals between 5% and 70% of a length L2 of drill bit 20, measured between proximal end 29 of shank 34 and distal tip 52 of drill shaft 30, such as between 10% to 50%.

Alternatively or additionally, for some applications, a length L3 of drill shaft 30, measured between proximal interface 40 of drill shaft 30 and distal tip 52 of drill shaft 30:
- is between 25 and 500 mm, such as between 30 and 300 mm, e.g., 150 mm, and/or
- equals between 30% and 95% of length L2 of drill bit 20, measured between proximal end of shank 34 and a distal tip 52 of drill shaft 30, such as between 50% and 90%.

Reference is made to FIG. 2B. For some applications, proximal interface 40 of drill shaft 30 is rotationally fixed to proximal electrically-conductive coupler 36 via distal electrically-conductive coupler 38. Alternatively or additionally, for some applications, distal electrically-conductive coupler 38 and drill shaft 30 comprise separate pieces that are coupled together at proximal interface 40 of drill shaft 30, such as shown in FIG. 2B.

Figure 19A:
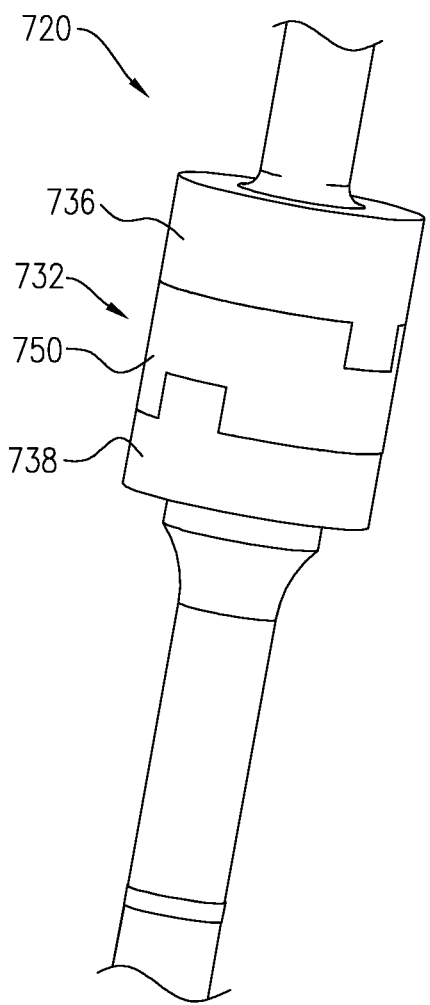
FIGS. 19A-B are schematic illustrations of still another drill bit, in accordance with an application of the present invention.
Figure 19B:
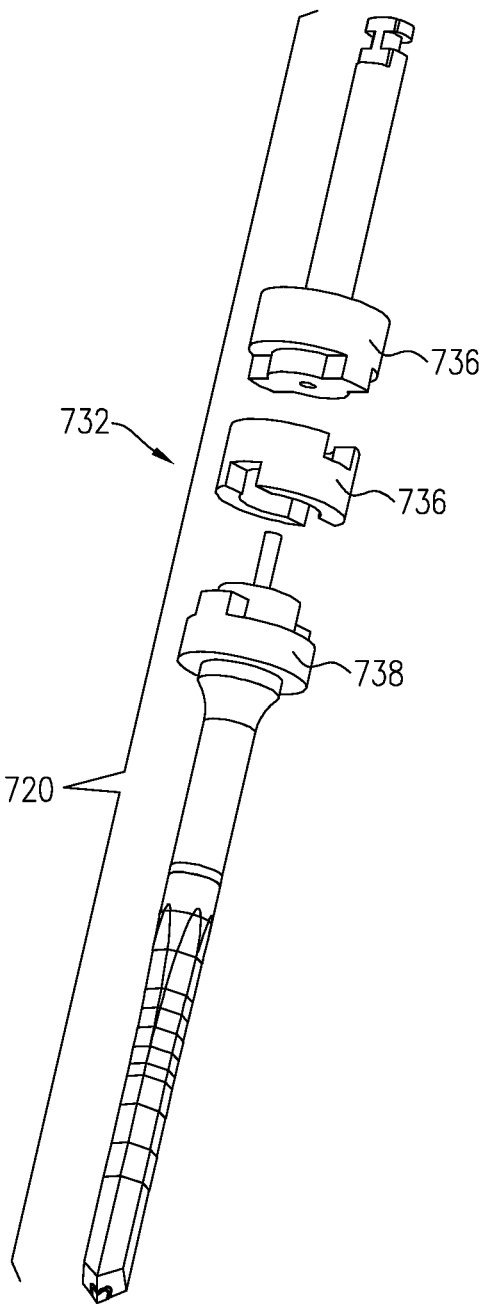

Reference is made to FIGS. 2A-B. For some applications, connector 32 comprises an insulator 50 that electrically isolates distal electrically-conductive coupler 38 from proximal electrically-conductive coupler 36. For some of these applications, distal electrically-conductive coupler 38 is rotationally fixed to proximal electrically-conductive coupler 36 via insulator 50 (optionally using a glue for the mechanical connection). For some of these applications, distal electrically-conductive coupler 38 is rotationally fixed to proximal electrically-conductive coupler 36 via insulator 50 via a lateral mechanical connection 53 (such as shown in FIG. 17), an axial mechanical connection 54 (such as shown in FIGS. 19A-B), and/or both lateral mechanical connection 53 and axial mechanical connection 54 (such as shown in FIGS. 2B, 4B, 6B, 6D, 6E, 6G, 13A-B, 13D, 15, 16, 20B, 20C, 21B, and 22B).

Reference is still made to FIGS. 2A-B. For some applications, insulator 50 comprises an isolation ring 72, which is configured to electrically isolate distal electrically-conductive coupler 38 and proximal electrically-conductive coupler 36 from each other.

For some applications, connector 32 and drill shaft 30 comprise separate pieces that are removably couplable to each other, such as during assembly of drill bit 20 before or during the surgical procedure, such as by a healthcare provider. Alternatively, connector 32 are removably or permanently coupled to each other during manufacture.

For some applications, proximal end portion 48 of electrically-conductive inner electrode 46 and proximal electrically-conductive coupler 36 of connector 32 comprise separate pieces that are directly coupled to each other (such as by press fitting or using a conductive glue).

Reference is made to FIG. 2B. For some applications, connector 32 further comprises an internal electrical contact 80, which is in electrical contact with proximal electrically-conductive coupler 36 and is electrically isolated from distal electrically-conductive coupler 38. Proximal end portion 48 of electrically-conductive inner electrode 46 is in electrical communication with proximal electrically-conductive coupler 36 via internal electrical contact 80.

For some of these applications, internal electrical contact 80 comprises a contact spring 82. For example, contact spring 82 may be in axial contact with proximal end portion 48 of electrically-conductive inner electrode 46, such as shown in FIG. 2B, as well as in FIGS. 13A, 13D, and 15, described hereinbelow.

Reference is made to FIGS. 2A-B and 4A-B. For some applications, distal-electrically-conductive external contact surface 62 surrounds 360 degrees of a central longitudinal axis 56 of connector 32. For some of these applications, distal-electrically-conductive external contact surface 62 faces at least partially radially outward, such as entirely radially outward, as shown in FIGS. 2A-B and 4A-B. Typically, in these applications, distal-electrically-conductive external contact surface 62 has a circular external cross-section. For example, the circular external cross-section may have a constant diameter along distal-electrically-conductive external contact surface 62, in which case distal-electrically-conductive external contact surface 62 is circularly cylindrical (as shown); or the circular cross-section may have a varying diameter along distal-electrically-conductive external contact surface 62, in which case distal-electrically-conductive external contact surface 62 may be conical and/or chamfered, such as in the configuration of distal-electrically-conductive external contact surface 1062 shown in FIGS. 22A-B, described hereinbelow, mutatis mutandis.

As used in the present application, including in the claims, "faces" means points and is oriented in a direction toward. For exampling, a surface faces proximally when the surface, which is perpendicular to a central longitudinal axis of the drill bit, is oriented in a proximal direction toward a proximal end of the drill bit. Similarly, a surface faces radially outward when the surface points away from the central longitudinal axis of the drill bit. A surface can face partially proximally and partially radially outward, or partially distally and partially radially outward, when the surface is angled with respect to the central longitudinal axis of the drill bit.

Reference is still made to FIGS. 2A-B and 4A-B. For some applications, proximal electrically-conductive coupler 36 is shaped so as to define a proximal-electrically-conductive external contact surface 60. For some of these applications, proximal-electrically-conductive external contact surface 60 surrounds 360 degrees of central longitudinal axis 56 of connector 32. For some of these applications, proximal-electrically-conductive external contact surface 60 faces at least partially radially outward, such as entirely radially outward. Typically, in these applications, proximal-electrically-conductive external contact surface 60 has a circular external cross-section. For example, the circular external cross-section may have a constant diameter along proximal-electrically-conductive external contact surface 60, in which case proximal-electrically-conductive external contact surface 60 is circularly cylindrical (such as shown in FIGS. 2A-B and 4A-B); or the circular cross-section may have a varying diameter along proximal-electrically-conductive external contact surface 60, in which case proximal-electrically-conductive external contact surface 60 may be conical and/or chamfered (configurations not shown, but similar to the configuration of distal-electrically-conductive external contact surface 1062 shown in FIGS. 22A-B).

Figure 5A:
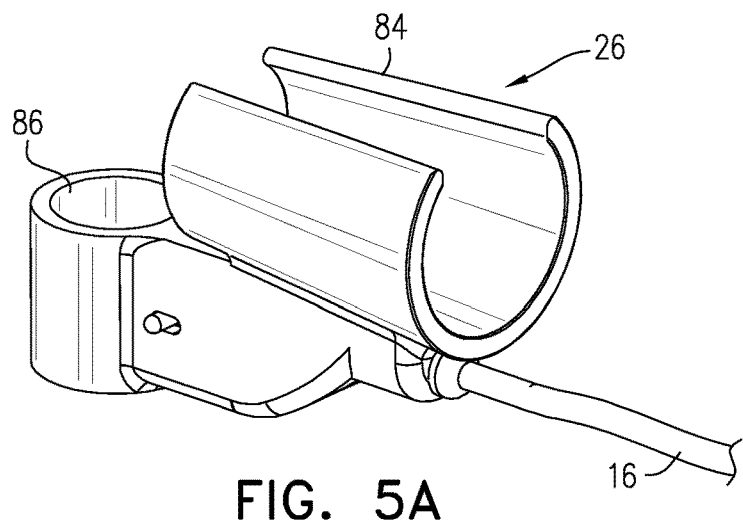
FIGS. 5A-C are schematic illustrations of a contact holder of the drill system of FIGS. 1A-B, in accordance with an application of the present invention.
Figure 5B:
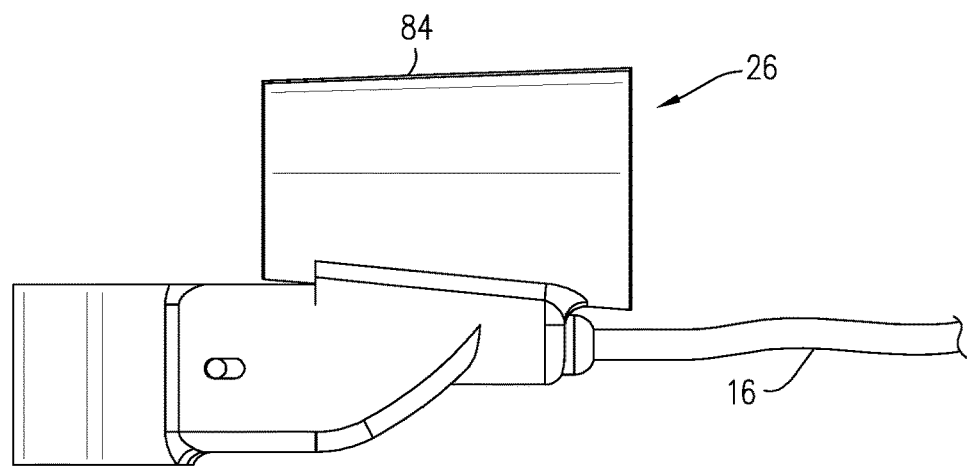
Figure 5C:
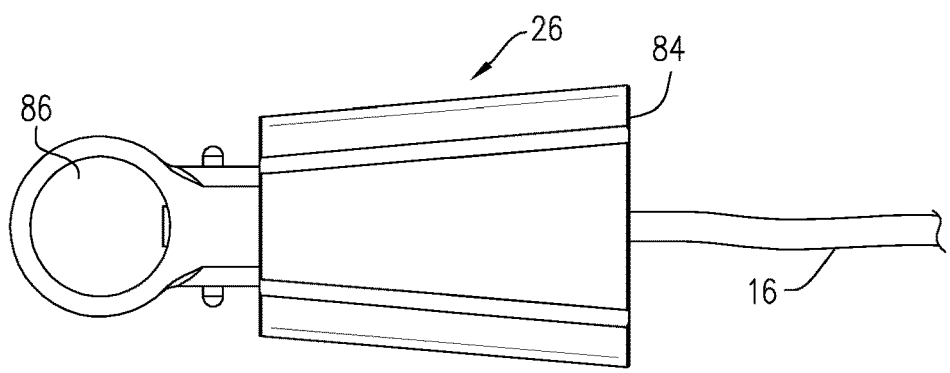

Reference is again made to FIGS. 1A-B, and is additionally made to FIGS. 5A-C, which are schematic illustrations of contact holder 26 of drill system 10, in accordance with an application of the present invention. Contact holder 26 is configured to transfer electrical signals from connector 32 of drill bit 20 to central unit 21, described hereinbelow with reference to FIG. 11.

For some applications, connector 32 is partially universal, in the sense that it can be mechanically coupled to any surgical drill (e.g., dental handpiece) commercially available without the need for special adaptations or modifications of the surgical drill. For these applications, connector 32 is typically not electrically coupled to the surgical drill, but instead only to central unit 21, described hereinbelow with reference to FIG. 11. Alternatively, the surgical drill is partially customized to convey electrical signals from drill bit 20, such as described hereinbelow with reference to FIGS. 10A-B.

Figure 6A:
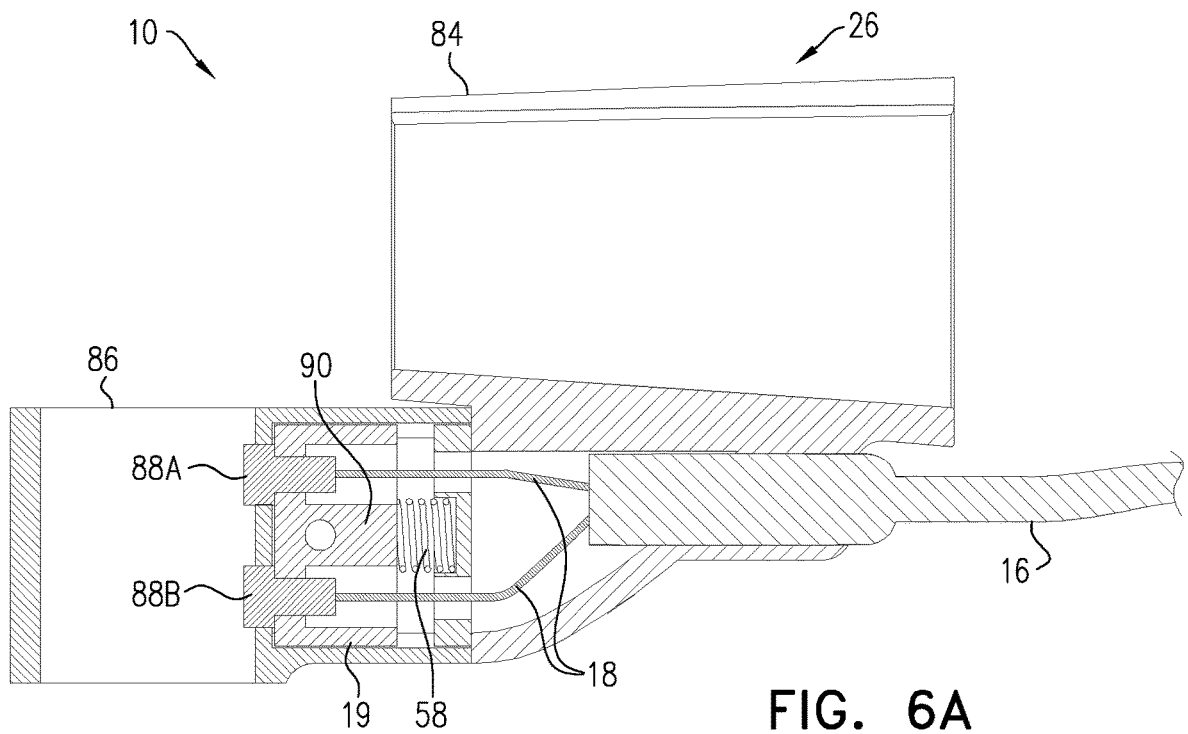
FIG. 6A is a cross-sectional view of the contact holder of FIGS. 5A-C, in accordance with an application of the present invention.
Figure 6B:
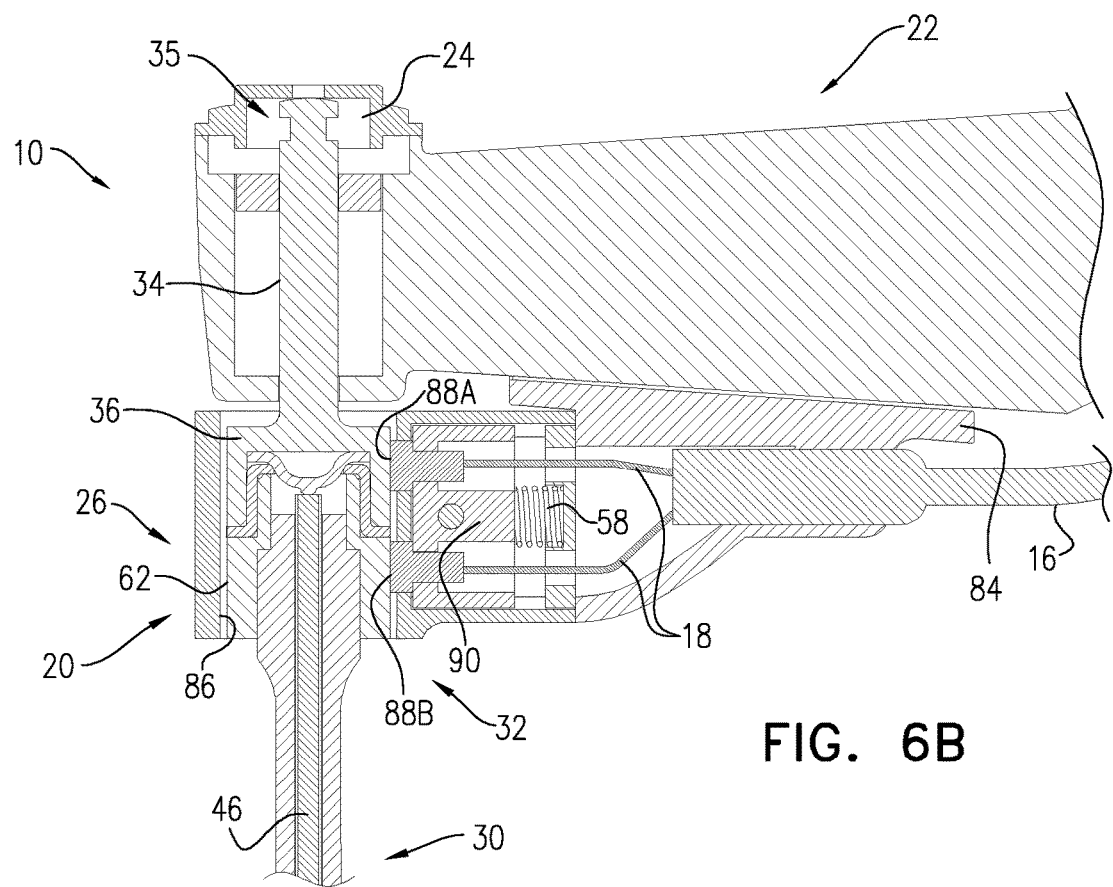
FIG. 6B is a cross-sectional view of the contact holder of FIGS. 5A-C, a portion of the drill bit of FIGS. 2A-B, and a portion of the surgical drill of FIGS. 1A-B, in accordance with an application of the present invention.

Reference is also made to FIG. 6A, which is a cross-sectional view of contact holder 26, and to FIG. 6B, which is a cross-sectional view of contact holder 26, a portion of drill bit 20, and a portion of surgical drill 22, in accordance with an application of the present invention.

Figure 6C:
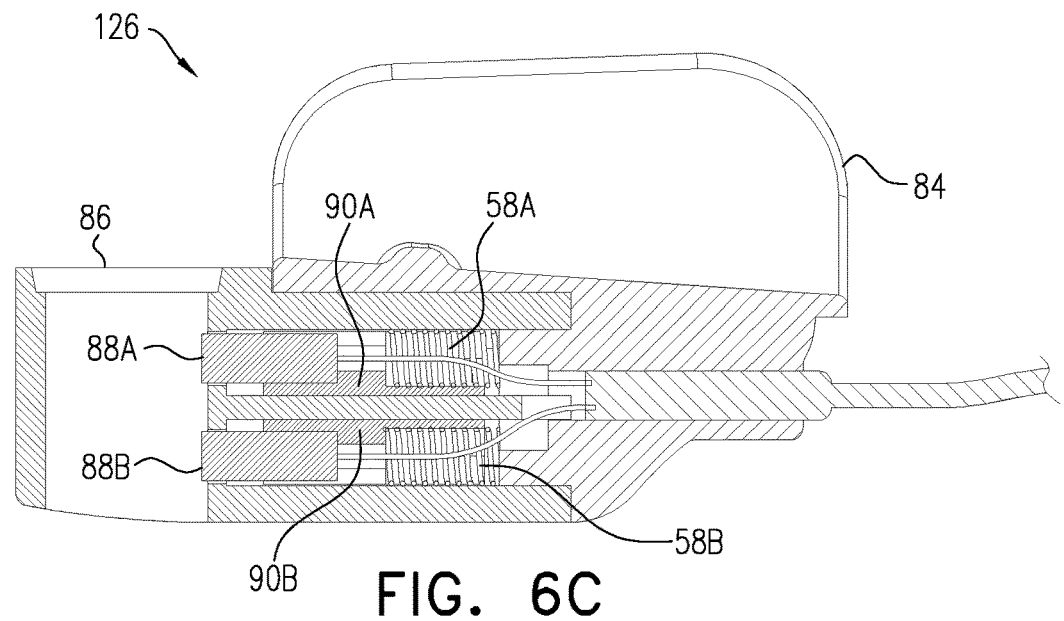
FIG. 6C is a cross-sectional illustration of another contact holder, in accordance with an application of the present invention.

Reference is also made to FIG. 6C, which is a cross-sectional illustration of a contact holder 126, in accordance with an application of the present invention. Other than as described below, contact holder 126 is identical to contact holder 26, and may implement any of the features thereof, mutatis mutandis.

Figure 6D:
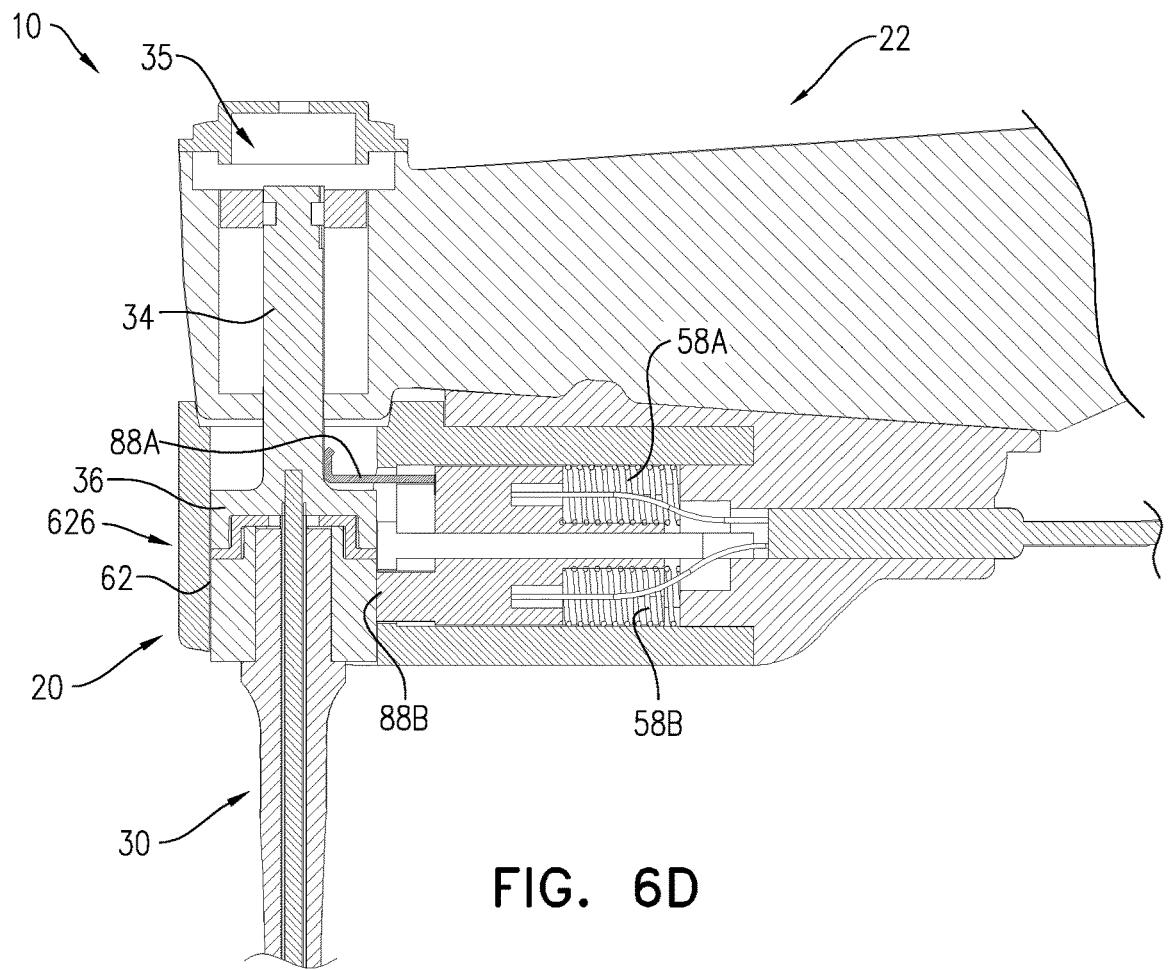
FIG. 6D is a cross-sectional illustration of yet another contact holder, a portion of the drill bit of FIGS. 2A-B, and a portion of the surgical drill of FIGS. 1A-B, in accordance with an application of the present invention.

Reference is also made to FIG. 6D, which is a cross-sectional illustration of a contact holder 626, in accordance with an application of the present invention. Other than as described below, contact holder 626 is identical to contact holder 126, and may implement any of the features thereof, mutatis mutandis.

Figure 6E:
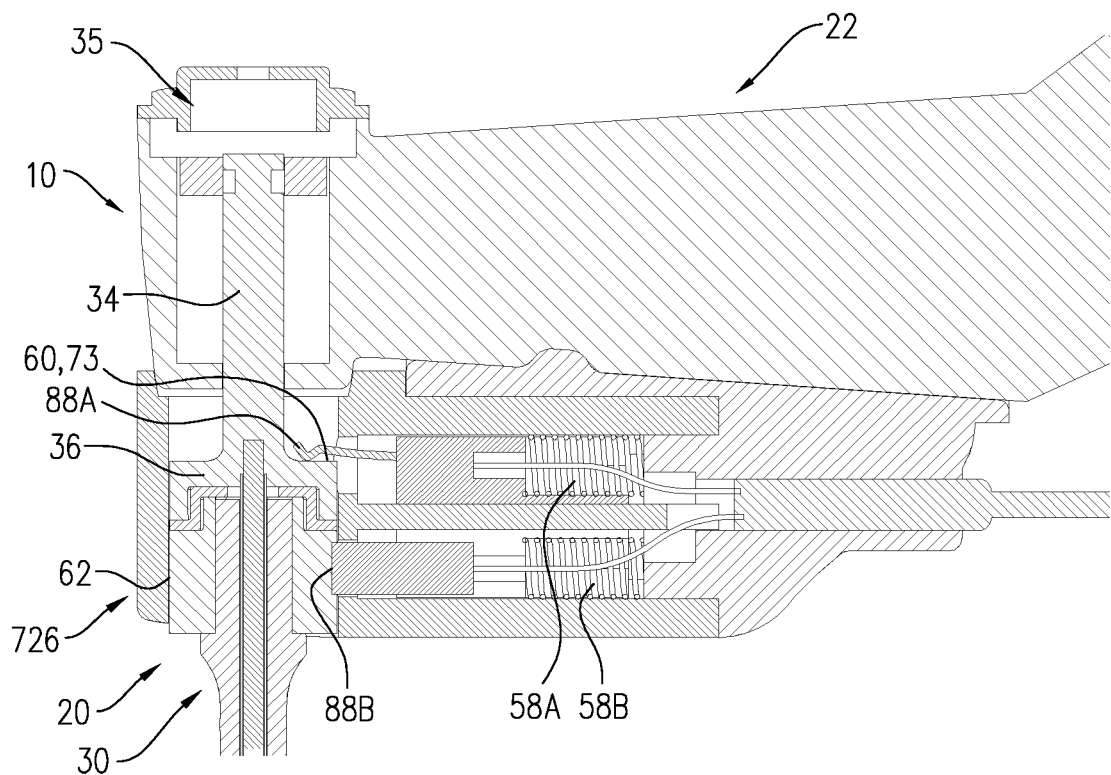
FIGS. 6E-F are illustrations of still another contact holder, in accordance with an application of the present invention.
Figure 6F:
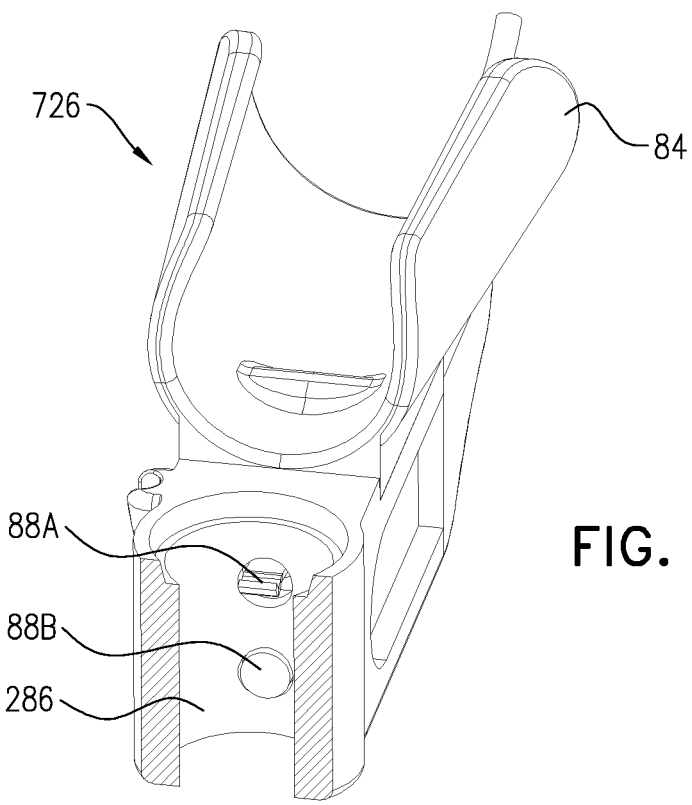

Reference is also made to FIGS. 6E-F, which are illustrations of a contact holder 726, in accordance with an application of the present invention. Other than as described below, contact holder 726 is identical to contact holder 126, and may implement any of the features thereof, mutatis mutandis.

Figure 6G:
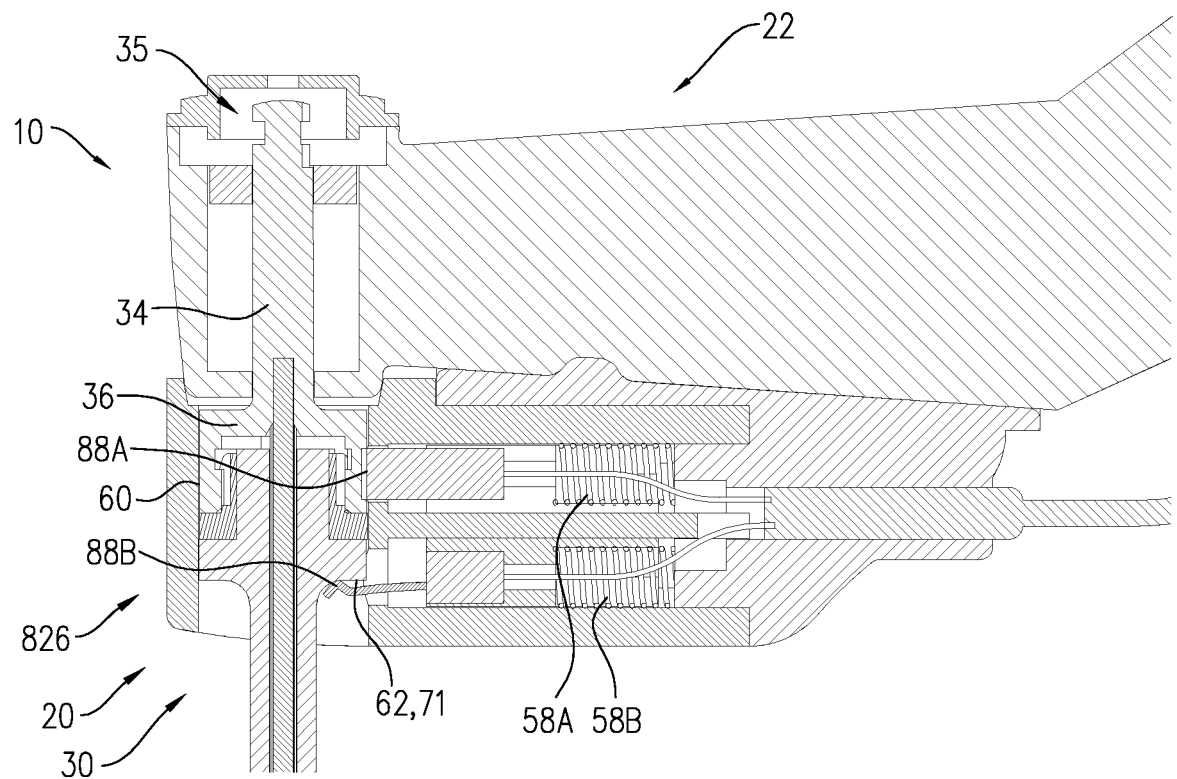
FIG. 6G is a cross-sectional illustration of another contact holder, in accordance with an application of the present invention.

Reference is also made to FIG. 6G, which is a cross-sectional illustration of a contact holder 826, in accordance with an application of the present invention. Other than as described below, contact holder 726 is identical to contact holder 126, and may implement any of the features thereof, mutatis mutandis.

Contact holders 26, 126, 626, 726, and 826 are configured to be mechanically coupled to surgical drill 22, such as shown, by way of example in FIGS. 1A-B, 6B, 6D, 6E, and 6G. For example, contact holder 26, 126, 626, 726, and 826 may comprise a clamp 84, which is configured to mechanically couple the contact holder to surgical drill 22. Alternatively, for example, contact holder 26, 126, 626, 726, and 826 may be screwed or otherwise temporarily or permanently coupled to surgical drill 22.

For some applications, such as shown in FIGS. 6A-G, contact holder 26, 126, 626, 726, and 826 comprises proximal and distal electrical connectors 88A and 88B. Distal electrical connectors 88A and 88B are configured to transfer the electrical signal between connector 32 and central unit 21, optionally via wires 18 and/or 16. For some applications, the wires are detachable from contact holder 26 and/or central unit 21. For some applications, connector 32 is wirelessly connected to central unit 21, rather than by wires 18 and 16, in which case at least some of the wires are typically not provided.

For some applications, such as shown in FIGS. 6A-G and 7, proximal and distal electrical connectors 88A and/or 88B comprise respective rigid contacts, such as carbon contacts or rigid contacts comprising other conductive materials, such as a conductive polymer.

In the configurations shown in FIGS. 6A-D and 7, proximal and distal electrical connectors 88A and 88B are shown as facing entirely radially inward, in order to make electrical contact with corresponding electrical contact surfaces that face entirely radially outward in this configuration. This orientation of proximal and distal electrical connectors 88A and 88B is also typically appropriate for configurations in which the corresponding electrical contact surfaces face only partially radially outward, e.g., are oriented obliquely, such as described hereinbelow with reference to FIGS. 22A-B. For configurations in which the electrical contact surfaces face distally or proximally, proximal and distal electrical connectors 88A and 88B are accordingly oriented in order to make electrical contact, such as described hereinbelow with reference to FIGS. 6E-G.

For some applications, such as shown in FIGS. 6A-C and 6E-G, contact holder 26, 126, 726, or 828 is configured to bring proximal and distal electrical connectors 88A and 88B in electrical contact with proximal-electrically-conductive external contact surface 60 and distal-electrically-conductive external contact surface 62, respectively, when connector 32 is received by contact holder 26, 126, 726, or 828, such as shown in FIG. 6B for contact holder 26, in FIGS. 6E-F for contact holder 726, and FIG. 6G for contact holder 826.

For some other applications, such as shown in FIG. 6D, contact holder 626 is configured, when connector 32 is received by contact holder 626, to bring proximal electrical connector 88A in electrical contact with shank 34 of connector 32. For these configurations, shank 34 is in electrical communication with proximal electrically-conductive coupler 36 (which may or may not be shaped so as to define proximal-electrically-conductive external contact surface 60). (Although proximal electrical connector 88A is shown as comprising a blade, such as described hereinbelow with reference to FIGS. 8A-B, proximal electrical connector 88A may alternatively have any of the other configurations described herein, mutatis mutandis.)

For some applications, such as shown in FIGS. 6E-F, contact holder 726 is configured, when connector 32 is received by contact holder 726, to bring proximal electrical connector 88A in electrical contact with a proximally-facing portion 73 of proximal-electrically-conductive external contact surface 60. For some of these applications, proximal electrical connector 88A comprises a blade, such as described hereinbelow with reference to FIGS. 8A-B. The natural springiness of the blade typically helps hold the blade in good electrical contact with proximally-facing portion 73 of proximal-electrically-conductive external contact surface 60. Alternatively, proximal electrical connector 88A may alternatively have any of the other configurations described herein, such as a brush or rigid contact, mutatis mutandis.

For some applications, such as shown in FIG. 6G, contact holder 826 is configured, when connector 32 is received by contact holder 826, to bring distal electrical connector 88B in electrical contact with a distally-facing portion 71 of distal-electrically-conductive external contact surface 62. For some of these applications, distal electrical connector 88B comprises a blade, such as described hereinbelow with reference to FIGS. 8A-B. The natural springiness of the blade typically helps hold the blade in good electrical contact with distally-facing portion 71 of distal-electrically-conductive external contact surface 62. Alternatively, distal electrical connector 88B may alternatively have any of the other configurations described herein, such as a brush or rigid contact, mutatis mutandis.

Although contact holders 726 and 826 are shown as comprising springs 58A and 58B, described hereinbelow with reference to FIGS. 6A-B, for some applications one or both of the springs is not provided, such as the spring that pushes on an electrical connector comprising a blade, which, as mentioned above, provides its own springiness.

Alternatively or additionally, for some applications, contact holder 26, 126, 626, 726, or 826 is configured, when connector 32 is received by contact holder 26 or 126, to bring distal electrical connector 88B in electrical contact with electrically-conductive outer electrode 44 (electrically-conductive outer electrode 44 is in electrical communication with distal electrically-conductive coupler 38) (configuration not shown).

For some applications, such as shown in FIGS. 6A-D, contact holder 26, 126, or 626 comprises one or more sliders 90 to which distal electrical connectors 88A and 88B are coupled. Contact holder 26, 126, or 626 further comprises one or more springs 58, which arranged and biased to push the one or more sliders 90, thereby, in the configurations shown in FIGS. 6A-C, bringing distal electrical connectors 88A and 88B in electrical contact with proximal-electrically-conductive external contact surface 60 and distal-electrically-conductive external contact surface 62, respectively, and ensuring a stable ongoing electrical connection. As mentioned above, in the configuration shown in FIG. 6D, proximal electrical connector 88A is brought into electrical contact with shank 34 of connector 32, rather than with proximal-electrically-conductive external contact surface 60.

In the configuration shown in FIGS. 6A-B, a single spring 58 pushes a single slider 90, which in turn pushes both distal electrical connectors 88A and 88B. In the configurations shown in FIGS. 6C-D, two respective springs 58A and 58B push two respective sliders 90A and 90B, which in turn push distal electrical connectors 88A and 88B, respectively.

Alternatively, for some applications, the configuration shown in FIGS. 6C and 6D are modified such that contact holder 126 does not comprise sliders 90, and springs 58 directly push distal electrical connectors 88A and 88B, respectively (configuration not shown).

Figure 7:
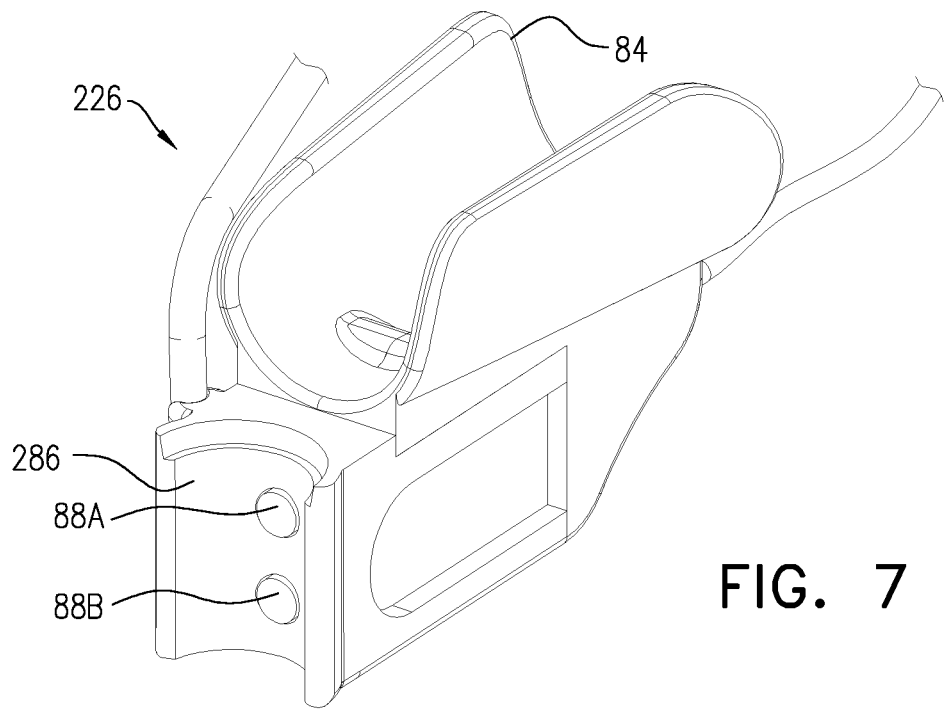
FIG. 7 is a schematic illustration of another contact holder, in accordance with an application of the present invention.

Reference is still made to FIGS. 6A-G and is additionally made to FIG. 7, which is a schematic illustration of a contact holder 226, in accordance with an application of the present invention. Other than as described below, contact holder 226 is similar to contact holders 26 and 126, described hereinabove with reference to FIGS. 6A-D, and may implement any of the features thereof, mutatis mutandis.

In the configurations shown in FIGS. 6A-G, contact holders 26 and 126 are shaped so as to define channel 86 for receiving connector 32.

Typically, channel 86 comprises a non-conductive material, such as plastic, in order to prevent a short-circuit between proximal electrically-conductive coupler 36 and distal electrically-conductive coupler 38 via channel 86. Alternatively, channel 86 comprises a conductive material, in which case electrical contact between channel 86 and connector 32 is prevented by an empty gap between these conductive elements, or by a gap between these conductive elements that is at least partially filled with a non-conductive material.

Channel 86 may, for example, be cylindrical or conical.

By contrast, in the configuration shown in FIG. 7, contact holder 226 is not shaped so as to define a channel, but instead is configured to be held against connector 32. By way of example and not limitation, contact holder 226 may be shaped so as to define an indentation 286 for receiving connector 32.

Contact holders 326, 426, and 526, described hereinbelow with reference to FIGS. 8A-B, 9A-B, and 10A-B, respectively, may optionally implement the non-channel features of contact holder 226, mutatis mutandis.

Figure 8A:
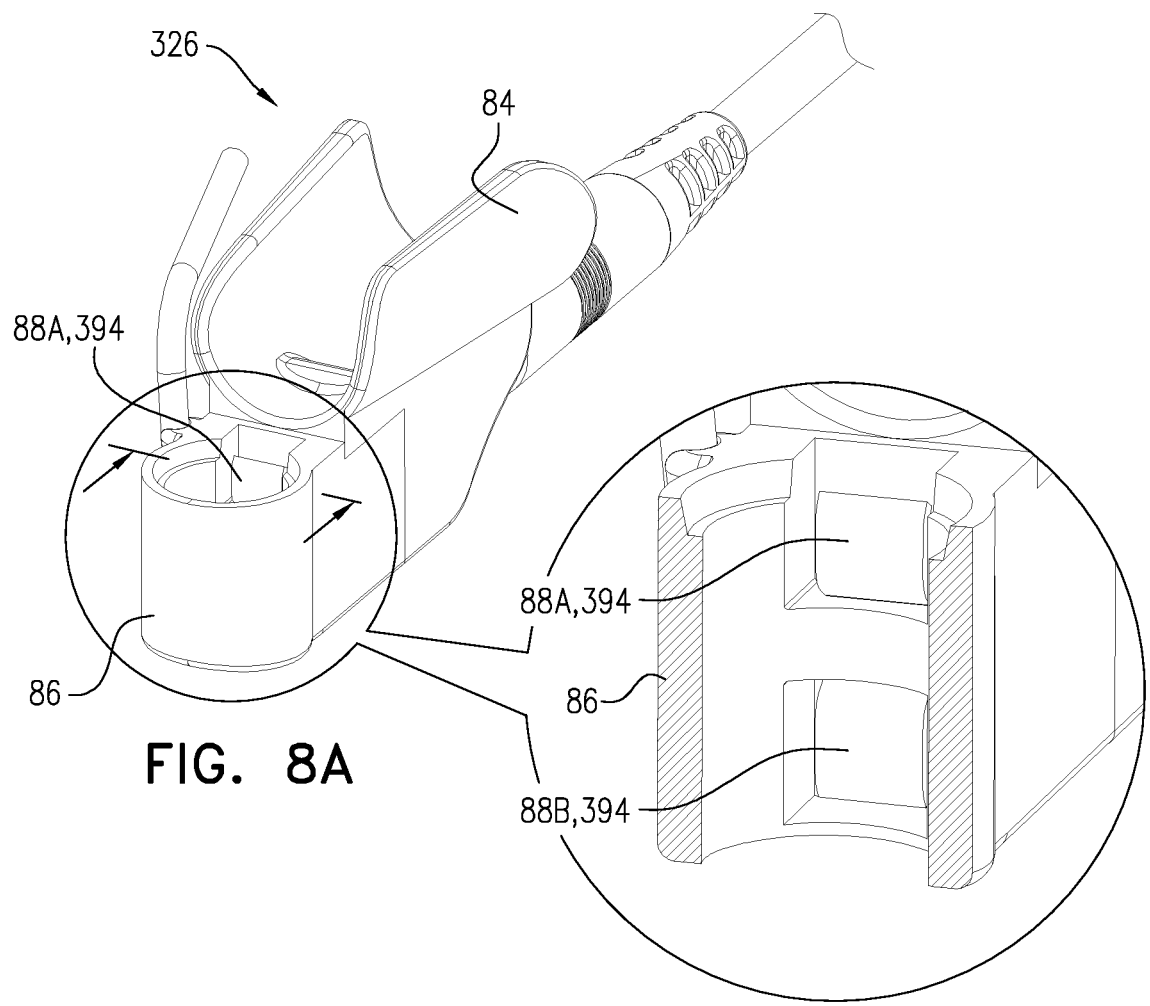
FIGS. 8A-B are schematic illustrations of yet another contact holder, in accordance with an application of the present invention.
Figure 8B:
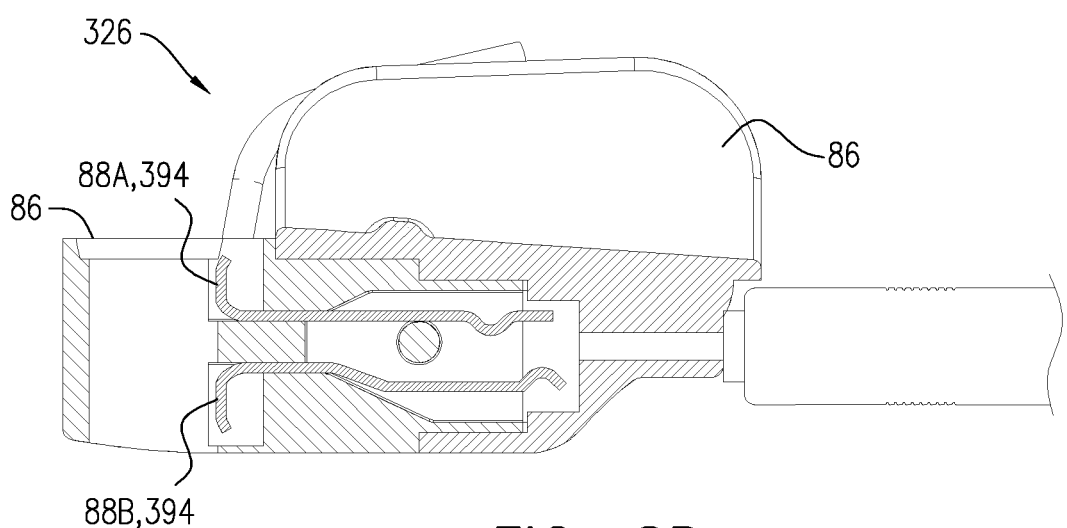

Reference is now made to FIGS. 8A-B, which are schematic illustrations of a contact holder 326, in accordance with an application of the present invention. Other than as described below, contact holder 326 is similar to contact holders 26 and 126, described hereinabove with reference to FIGS. 6A-D, and may implement any of the features thereof, mutatis mutandis, and/or any of the features of contact holders 626, 726, and/or 826, mutatis mutandis. In this configuration, proximal electrical connector 88A and/or distal electrical connector 88B comprise respective blades 394. Typically, blades 394 are springy and ensure the continuous electrical contact of electrical connectors 88A and 88B with proximal-electrically-conductive external contact surface 60 and distal-electrically-conductive external contact surface 62, respectively. There can be several electrical points of contact per external surfaces. In this configuration, springs 58 are typically not provided, although they may be provided. In addition, in this configuration, wires 18 are typically not provided, although they may be provided.

Figure 9A:
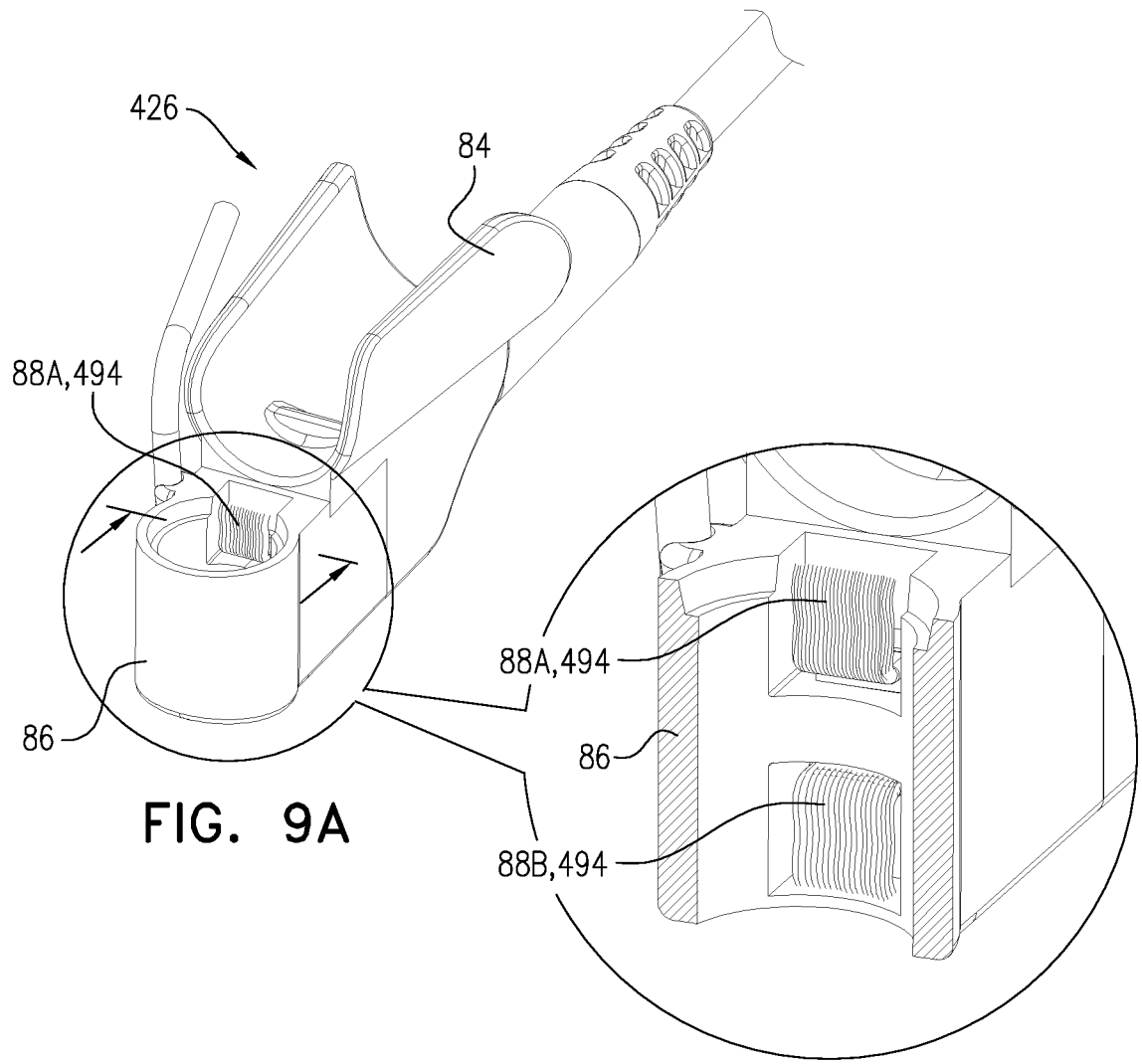
FIGS. 9A-B are schematic illustrations of still another contact holder, in accordance with an application of the present invention.
Figure 9B:
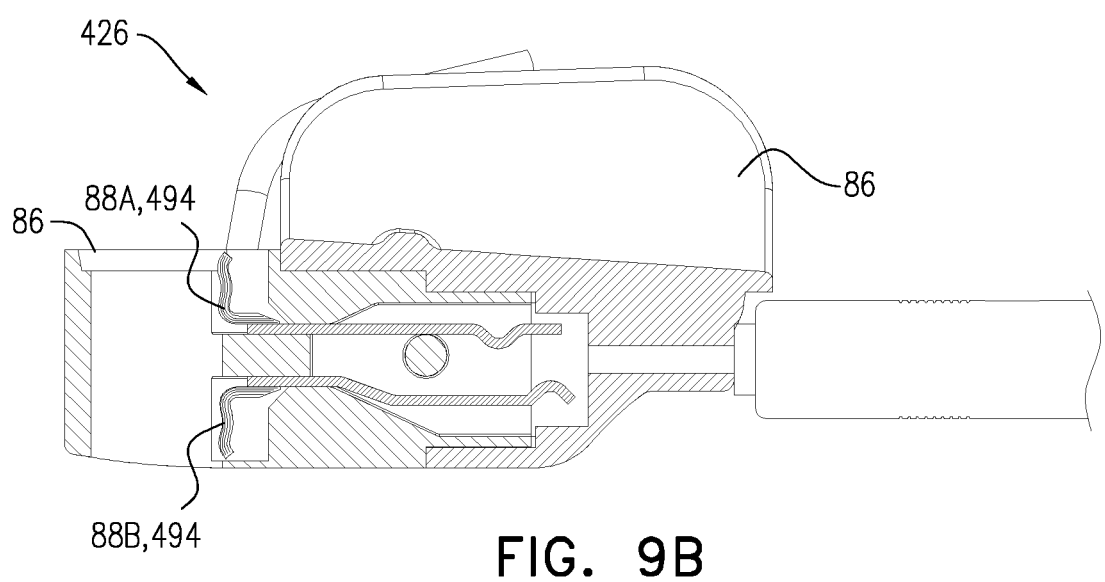

Reference is now made to FIGS. 9A-B, which are schematic illustrations of a contact holder 426, in accordance with an application of the present invention. Other than as described below, contact holder 426 is similar to contact holders 26 and 126, described hereinabove with reference to FIGS. 6A-D, and may implement any of the features thereof, mutatis mutandis, and/or any of the features of contact holders 626, 726, and/or 826, mutatis mutandis. In this configuration, proximal electrical connector 88A and/or distal electrical connector 88B comprise respective brushes 494. In this configuration, springs 58 are typically not provided, although they may be provided. In addition, in this configuration, wires 18 are typically not provided, although they may be provided.

In any of the configurations described herein comprising more than one electrical connector, the electrical connectors may comprise rigid contacts, blades, and/or brushes in any combination.

Figure 10A:
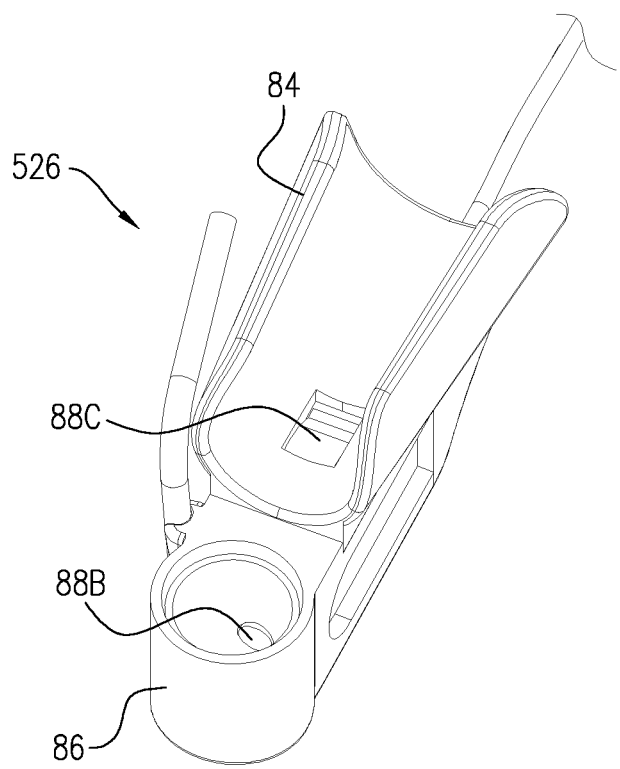
FIGS. 10A-B are schematic illustrations of another contact holder, in accordance with an application of the present invention.
Figure 10B:
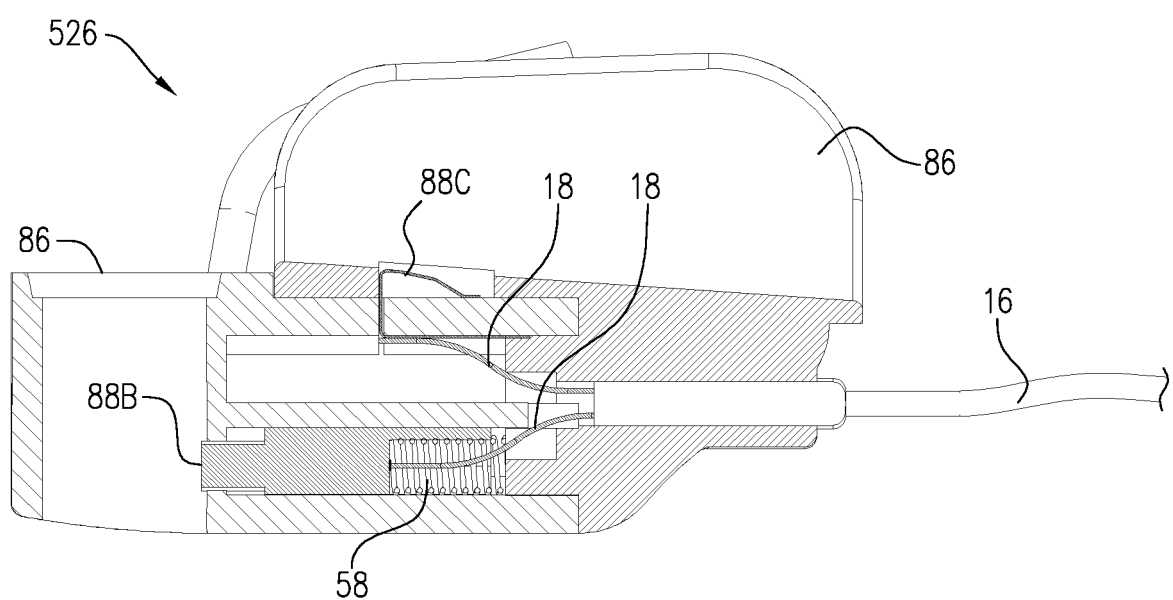

Reference is again made to FIGS. 1A-B, 2A-B, and 4A-B, and is also made to FIGS. 10A-B, which are schematic illustrations of a contact holder 526, in accordance with an application of the present invention. Other than as described below, contact holder 526 is similar to contact holders 26, 126, and 626, described hereinabove with reference to FIGS. 6A-D, and may implement any of the features thereof, mutatis mutandis, and/or any of the features of contact holders 626, 726, and/or 826, mutatis mutandis. Contact holder 626 may also optionally implement any of the features of contact holders 326 and/or 426, described hereinabove with reference to FIGS. 8A-B and 9A-B, respectively, mutatis mutandis.

For some applications, proximal electrically-conductive coupler 36 is in electrical communication with shank 34 (see FIGS. 2A-B and 4A-B). For some of these applications, shank 34 of connector 32 is configured to be electrically connected to surgical drill 22 (shown in FIGS. 1A-B).

For some applications, contact holder 526 comprises distal electrical connector 88B. Contact holder 526 is configured to bring distal electrical connector 88B in electrical contact with distal-electrically-conductive external contact surface 62 when connector 32 is received by contact holder 526. Contact holder 526 further comprises a surgical drill electrical connector 88C, which is configured to be electrically coupled to surgical drill 22. Surgical drill 22, typically via chuck 24 thereof, is configured to couple shank 34 of connector 32 in electrical communication with surgical drill electrical connector 88C, when shank 34 is coupled to surgical drill 22 and connector 32 is received by contact holder 526. In this configuration, contact holder typically does not comprise proximal electrical connector 88A, because electrical connection with proximal electrically-conductive coupler 36 is made via shank 34 rather than via a proximal-electrically-conductive external contact surface 60. (In this configuration, proximal electrically-conductive coupler 36 may or may not be shaped so as to define proximal-electrically-conductive external contact surface 60.)

The various configurations of the contact holders described herein may be implemented in any combination, mutatis mutandis, for example depending on the configuration of the proximal-electrically-conductive external contact surface and/or distal-electrically-conductive external contact surface of connector which the contact holder is configured to receive.

Figure 11:
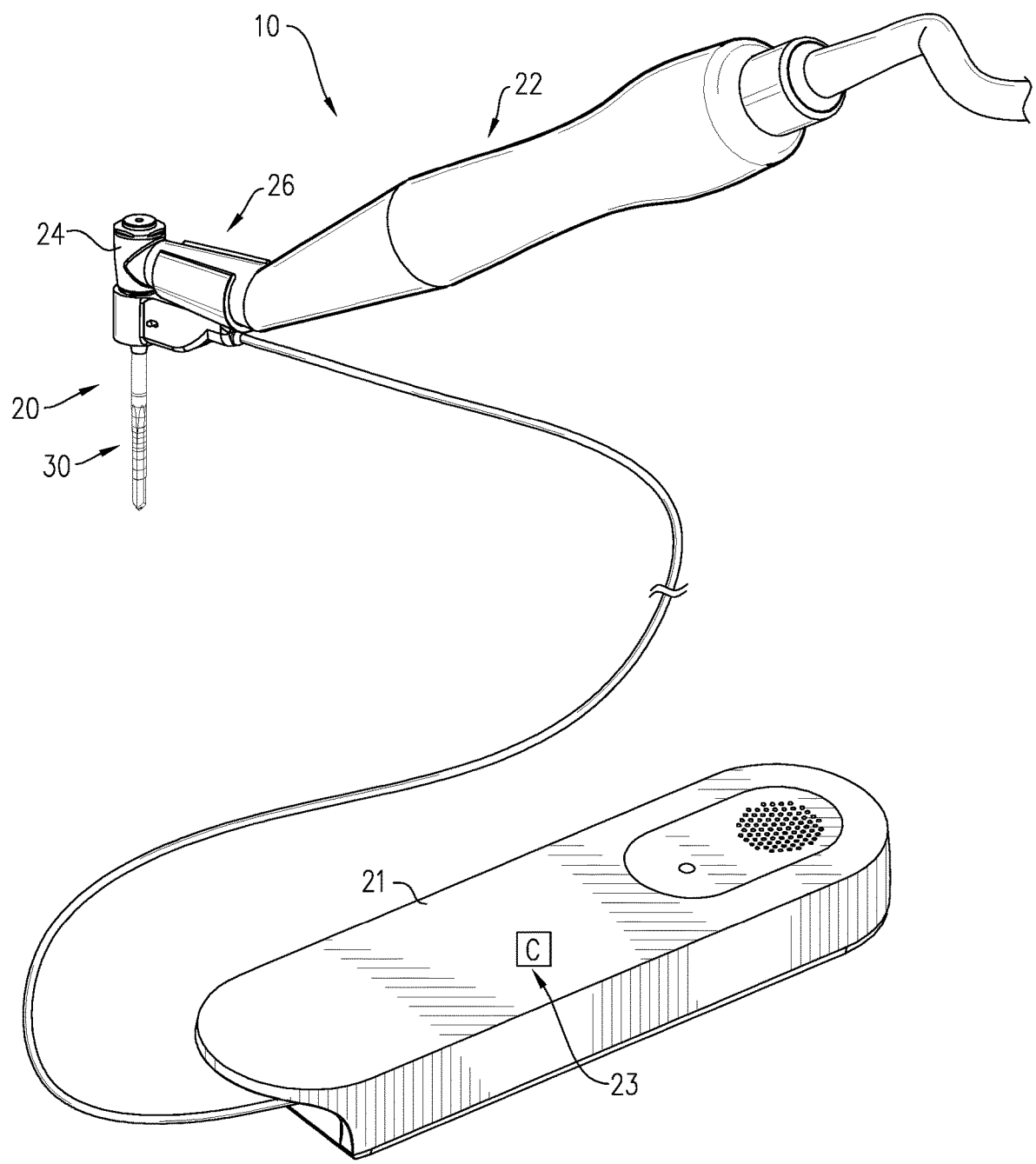
FIG. 11 is a schematic illustration of the drill system of FIGS. 1A-B further comprising a central unit, in accordance with an application of the present invention.

Reference is now made to FIG. 11, which is a schematic illustration of drill system 10 further comprising central unit 21, in accordance with an application of the present invention. Drill system 10 may or may not comprise surgical drill 22. Central unit 21 comprises circuitry 23 that is configured to supply power to electrically-conductive outer electrode 44 and/or electrically-conductive inner electrode 46 of drill bit 20, in order to measure continuously an electrical characteristic representative of the capacity of the tissue structure for allowing the passage of the electrical current between the electrodes. Central unit 21 is further configured to process the measured characteristics received from drill bit 20 and provides real-time feedback. The feedback can be a signal perceived by a human user, e.g., audio and/or visual and/or tactile. Alternatively, the feedback can be an electronic signal delivered to the control unit of an assistance device, e.g., a power drill, a navigation system, or a robotic system. The aforementioned electrical characteristic representative of the capacity of the tissue structure for allowing the passage of the electrical current can be impedance, measured via for example voltage or current.

Central unit 21 may be configured to use drill bit 20 to sense electrical properties of the tissue penetrated by drill bit 20, such as impedance, change in impedance, voltage, or change in voltage. For example, central unit 21 may comprise an impedance meter for measuring the impedance and/or change in impedance.

The sensed electrical properties may be used by the operator of surgical drill 22 to monitor the penetration of drill bit 20 into anatomical structures and, in particular, bone structures having at least two different electrical impedance areas, such as bone (e.g., cortical bone) and soft tissue. In addition, the sensed electrical properties enable the bipolar measurement of local electrical properties of the tissue, which are more difficult, if not impossible, to measure using a single electrode on the drill bit and a remote external skin return electrode, as is known in the impedance measurement drill art.

Figure 12A:
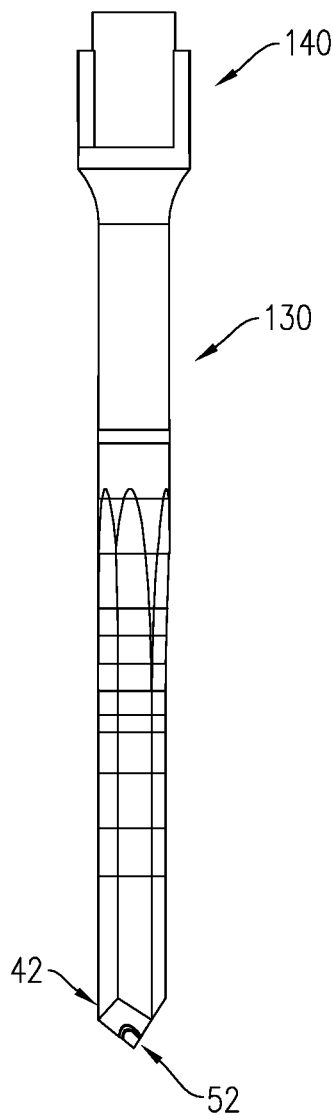
FIGS. 12A-B are schematic illustrations of a drill shaft, in accordance with an application of the present invention.
Figure 12B:
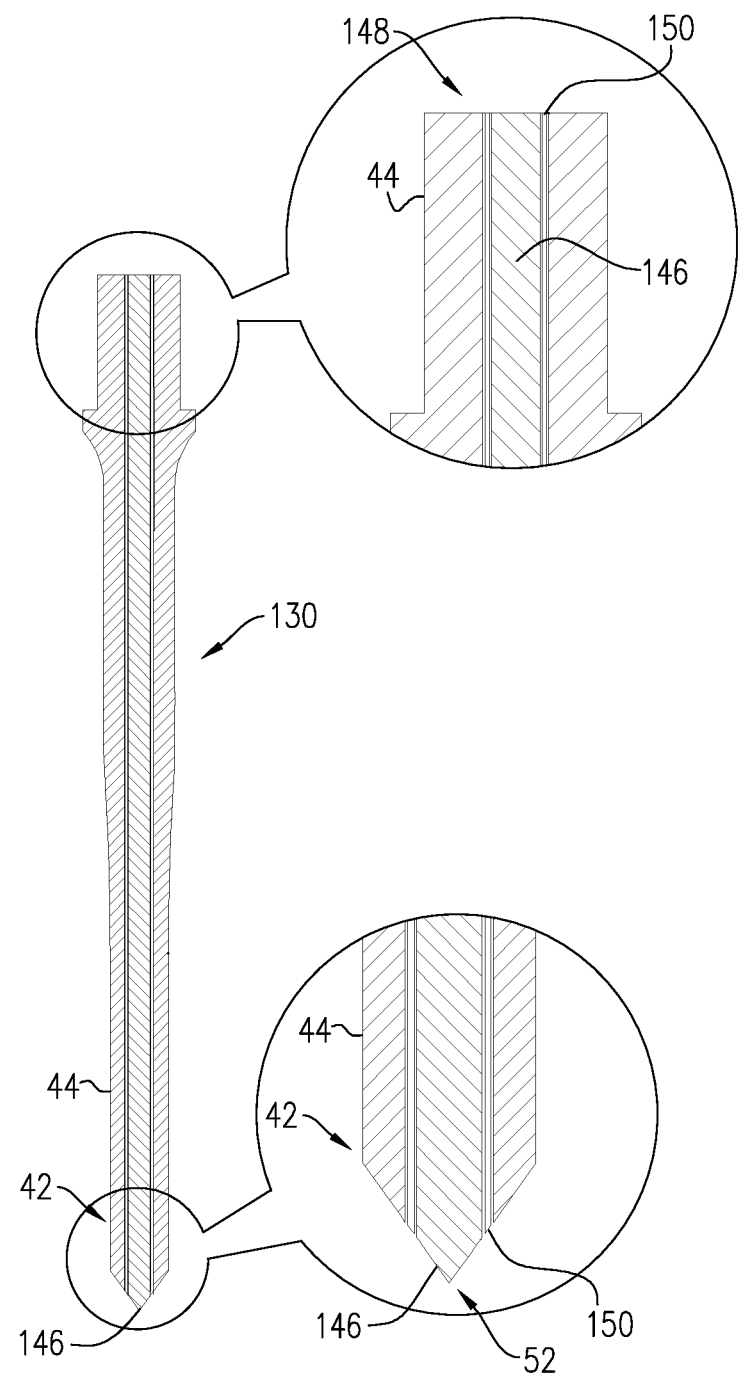

Reference is now made to FIGS. 12A-B, which are schematic illustrations of a drill shaft 130, in accordance with an application of the present invention. Drill shaft 130 is one implementation of drill shaft 30 described hereinabove, and may implement any of the features thereof, mutatis mutandis. In this configuration, an electrically-conductive inner electrode 146 of drill shaft 130 is flush with a proximal end of drill shaft 130.

Reference is now made to FIGS. 13A-D, which are schematic illustrations of a drill shaft 230, in accordance with respective applications of the present invention. Drill shaft 230 is one implementation of drill shaft 30 described hereinabove, and may implement any of the features thereof, mutatis mutandis. In this configuration, an electrically-conductive inner electrode 246 of drill shaft 230 protrudes proximally from a proximal end of drill shaft 230.

Figure 13A:
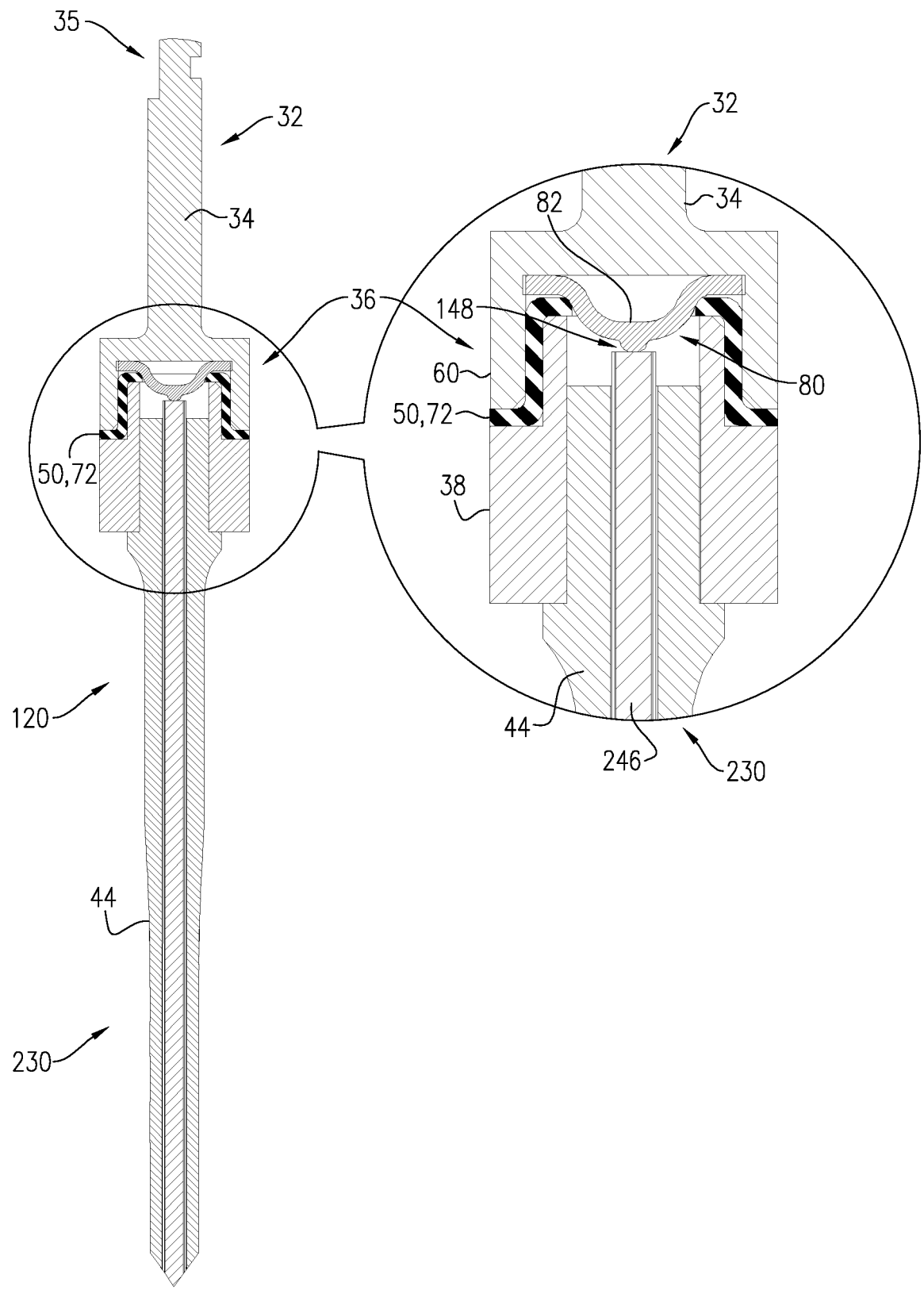
FIGS. 13A-D are schematic illustrations of another drill shaft, in accordance with respective applications of the present invention.

For some applications, such as shown in FIG. 13A, electrically-conductive inner electrode 246 is recessed within distal electrically-conductive coupler 38 of connector 32. In other words, a distal end of electrically-conductive inner electrode 246 is disposed more distally than a distal end of distal electrically-conductive coupler 38 of connector 32.

Figure 13B:
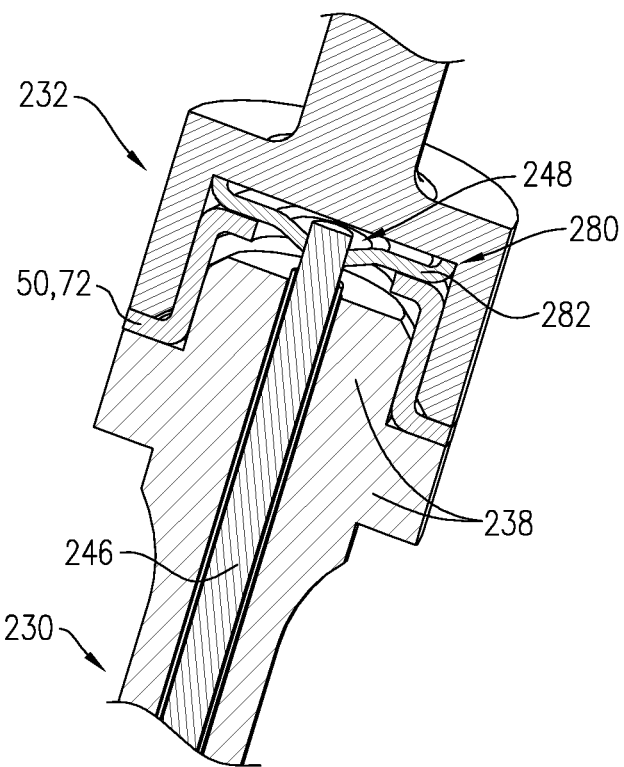
Figure 13C:
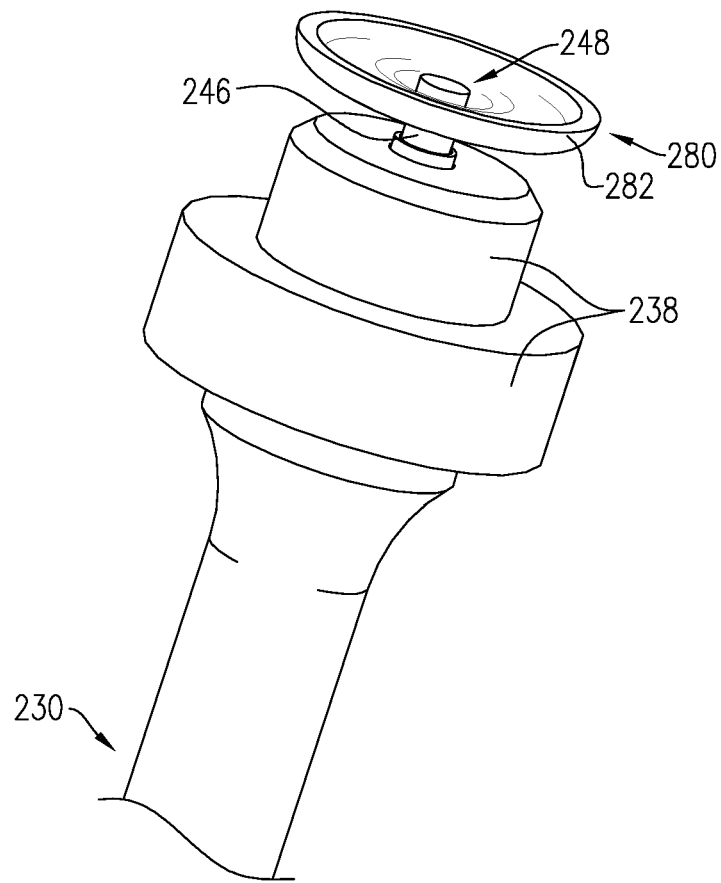

For other applications, such as shown in FIGS. 13B-C, electrically-conductive inner electrode 246 protrudes proximally from a distal electrically-conductive coupler 238 of a connector 232. In other words, a distal end of distal electrically-conductive coupler 238 of connector 232 is disposed more distally than a distal end of electrically-conductive inner electrode 246.

Figure 13D:
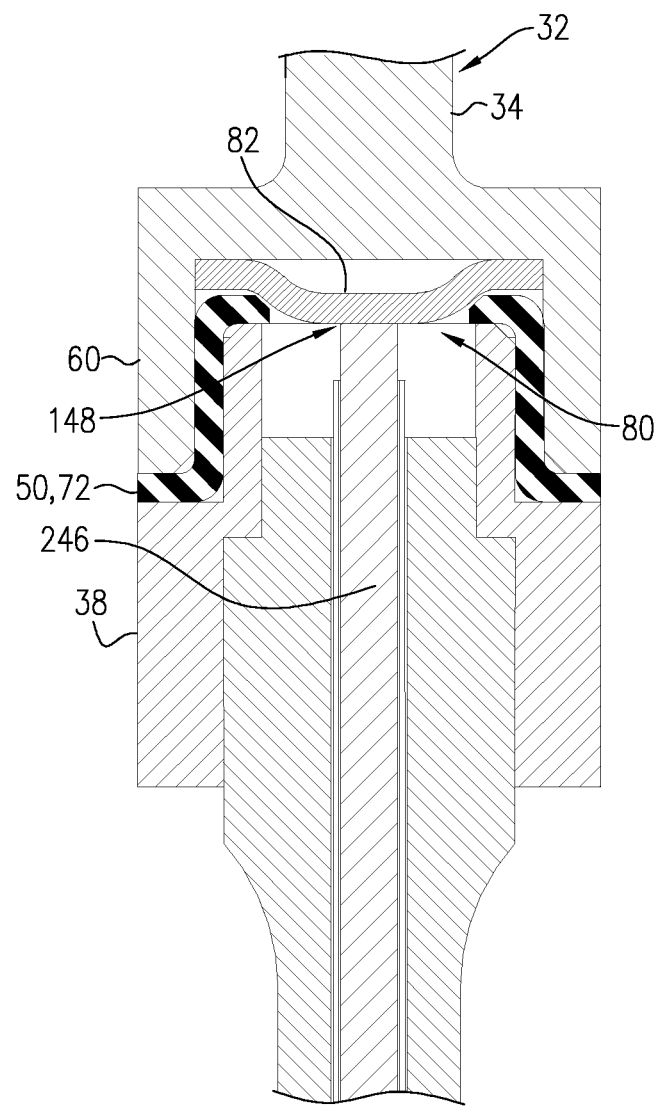

For still other applications, such as shown in FIG. 13D, electrically-conductive inner electrode 246 is flush with distal electrically-conductive coupler 38 or 238 of connector 32 or 232.

Reference is again made to FIGS. 13B-C. For some applications, connector 232 comprises an internal electrical contact 280, which comprises a contact spring 282. Contact spring 282 is in lateral contact with a proximal end portion 248 of electrically-conductive inner electrode 246.

Figure 14A:
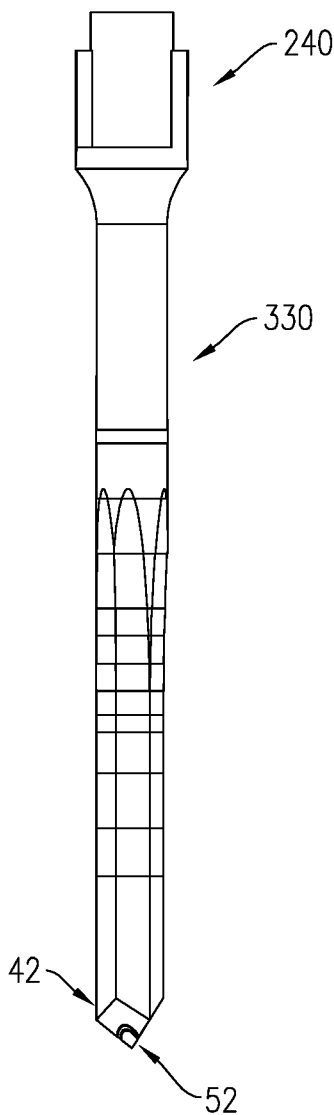
FIGS. 14A-B are schematic illustrations of yet another drill shaft, in accordance with respective applications of the present invention.
Figure 14B:
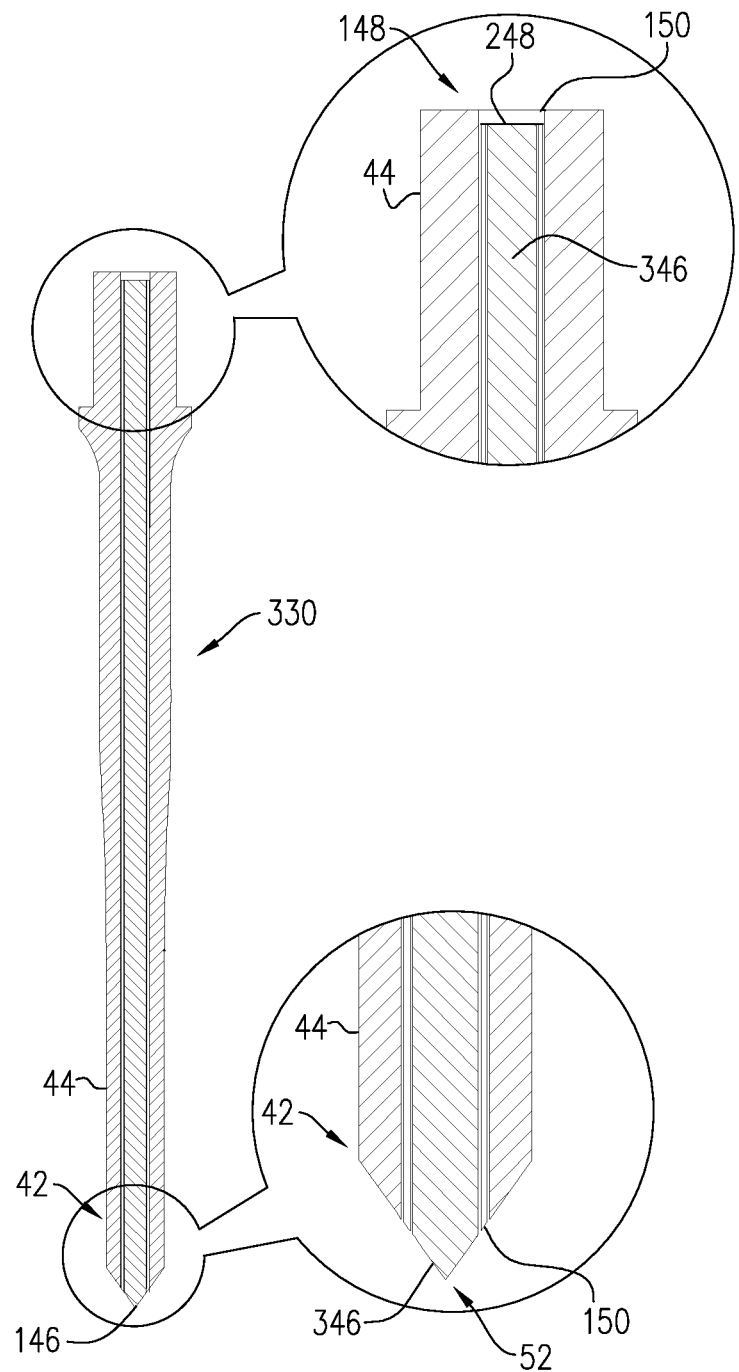
Figure 15:
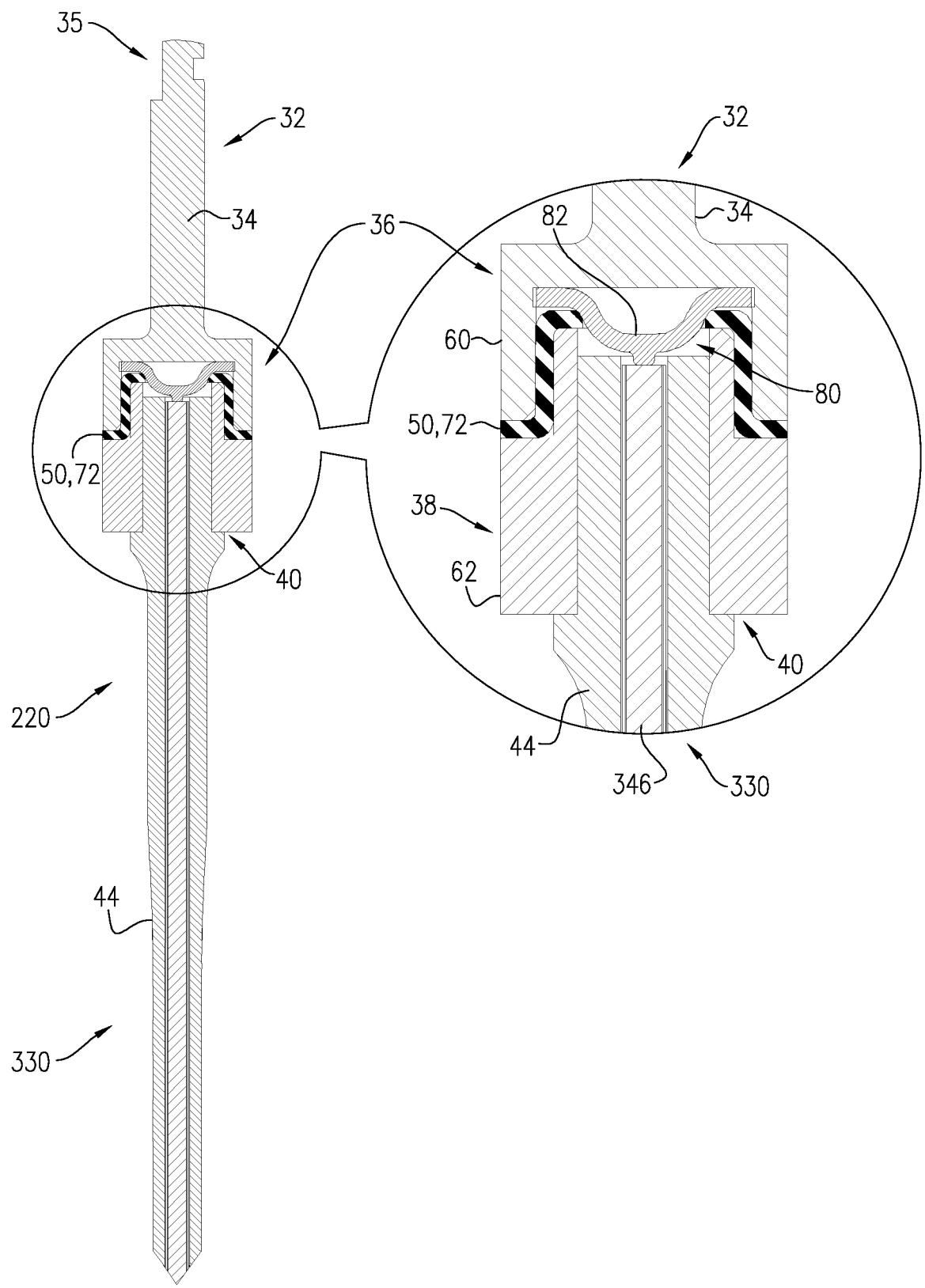
FIG. 15 is a schematic illustration of the drill shaft of FIGS. 14A-B, further comprising a connector, in accordance with respective applications of the present invention.

Reference is now made to FIGS. 14A-B and 15, which are schematic illustrations of a drill shaft 330, in accordance with respective applications of the present invention. Drill shaft 330 is one implementation of drill shaft 30 described hereinabove, and may implement any of the features thereof, mutatis mutandis. In this configuration, an electrically-conductive inner electrode 346 of drill shaft 330 is recessed within a proximal end of drill shaft 330.

Figure 16:
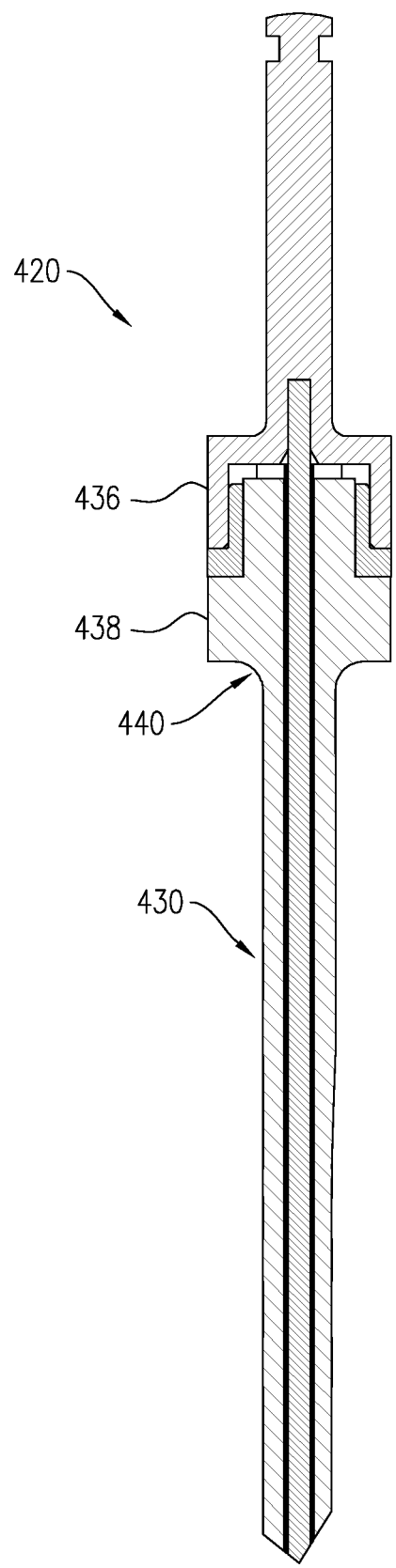
FIG. 16 is a schematic illustration of a drill bit, in accordance with an application of the present invention.
Figure 17:
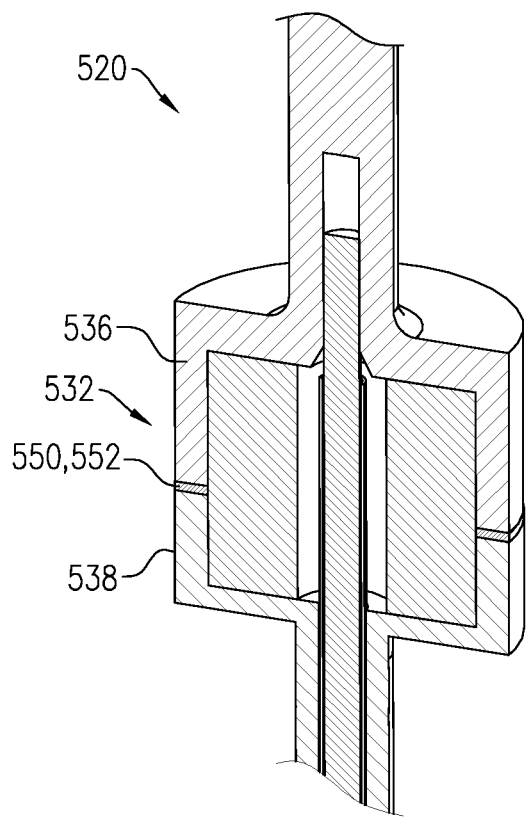
FIG. 17 is a schematic cross-sectional illustration of another drill bit, in accordance with an application of the present invention.

Reference is now made to FIG. 16, which is a schematic illustration of a drill bit 420, in accordance with an application of the present invention. Other than as described below, drill bit 420 is generally similar to drill bit 20, described hereinabove with reference to FIGS. 1A-4B, and may implement any of the features thereof, as well as any of the features of the other drill bits described herein, mutatis mutandis.

A distal electrically-conductive coupler 438 is integral to a drill shaft 430 of drill bit 420 at a proximal interface 440 of drill shaft 430 that is rotationally fixed with respect to a proximal electrically-conductive coupler 436 and configured to transfer torque from proximal electrically-conductive coupler 436 to drill shaft 430. This is also the case for the configurations shown in FIG. 13B-D, described hereinabove, and FIGS. 17, 18A-B, 19A-B, and 20A-C, described hereinbelow.

Reference is now made to FIG. 17, which is a schematic cross-sectional illustration of a drill bit 520, in accordance with an application of the present invention. Other than as described below, drill bit 520 is generally similar to drill bit 20, described hereinabove with reference to FIGS. 1A-4B, and may implement any of the features thereof, as well as any of the features of the other drill bits described herein, mutatis mutandis.

A connector 532 of drill bit 520 comprises an insulator 550 that electrically isolates a distal electrically-conductive coupler 538 from a proximal electrically-conductive coupler 536. Insulator 550 comprises a coating or a non-conductive glue 552.

Figure 18A:
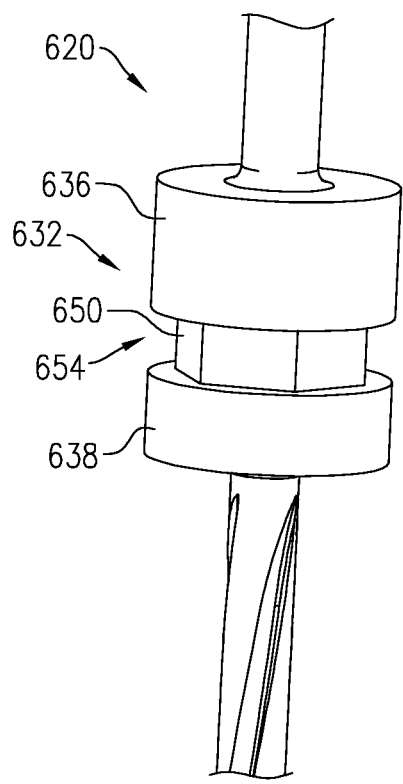
FIGS. 18A-B are schematic illustrations of yet another drill bit, in accordance with an application of the present invention.
Figure 18B:
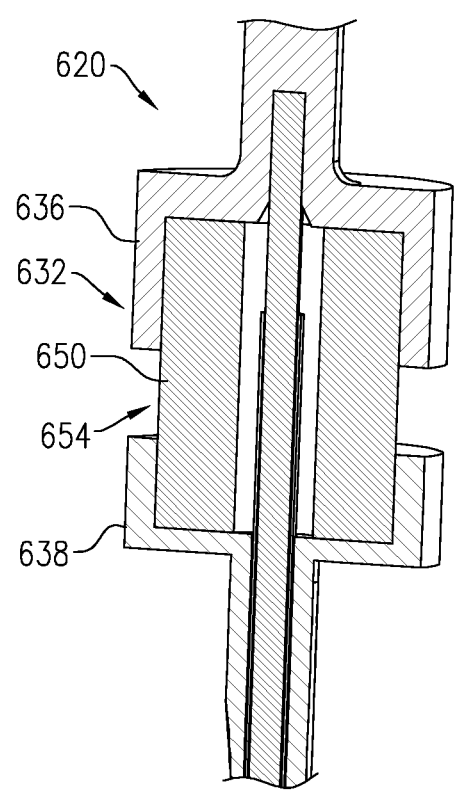

Reference is now made to FIGS. 18A-B, which are schematic illustrations of a drill bit 620, in accordance with an application of the present invention. Other than as described below, drill bit 620 is generally similar to drill bit 20, described hereinabove with reference to FIGS. 1A-4B, and may implement any of the features thereof, as well as any of the features of the other drill bits described herein, mutatis mutandis.

A connector 632 of drill bit 620 comprises a non-conductive spacer 650 that electrically isolates a distal electrically-conductive coupler 638 from a proximal electrically-conductive coupler 636. Connector 632 is configured to electrically isolate distal electrically-conductive coupler 638 from proximal electrically-conductive coupler 636 in part by defining an empty gap 654 between distal electrically-conductive coupler 638 and proximal electrically-conductive coupler 636. Empty gap 654 may extend entirely around connector 632, as shown, or may extend around only a portion of connector 632, in which case empty gap 654 may optionally comprise two or more empty gaps 654. Empty gap 654 is typically located around the periphery of connector 632. Typically, non-conductive spacer 650 provides mechanical coupling between distal electrically-conductive coupler 638 and proximal electrically-conductive coupler 636.

Reference is now made to FIGS. 19A-B, which are schematic illustrations of a drill bit 720, in accordance with an application of the present invention. Other than as described below, drill bit 720 is generally similar to drill bit 20, described hereinabove with reference to FIGS. 1A-4B, and may implement any of the features thereof, as well as any of the features of the other drill bits described herein, mutatis mutandis.

A connector 732 of drill bit 720 comprises an insulator 750 that electrically isolates a distal electrically-conductive coupler 738 from a proximal electrically-conductive coupler 736. In this configuration, distal electrically-conductive coupler 738 is rotationally fixed to proximal electrically-conductive coupler 736 via insulator 750 via an axial mechanical connection.

Reference is now made to FIGS. 20A-B and 20C, which are schematic illustrations of respective configurations a drill bit 820, in accordance with respective applications of the present invention. Other than as described below, drill bit 820 is generally similar to drill bit 20, described hereinabove with reference to FIGS. 1A-4B, and may implement any of the features thereof, as well as any of the features of the other drill bits described herein, mutatis mutandis.

A connector 832 of drill bit 820 comprises a distal electrically-conductive coupler 838 and a proximal electrically-conductive coupler 836, which is shaped so as to define a proximal-electrically-conductive external contact surface 860. Connector 832 further comprises an insulator 850 that electrically isolates distal electrically-conductive coupler 838 from proximal electrically-conductive coupler 836. Insulator 850 may implement any of the features of the other insulators described herein, mutatis mutandis.

Proximal-electrically-conductive external contact surface 860 faces at least partially proximally, such as entirely proximally, as shown. For some of these applications, proximal-electrically-conductive external contact surface 860 surrounds 360 degrees of a central longitudinal axis of connector 832.

Typically, distal electrically-conductive coupler 838 is shaped so as to define a distal-electrically-conductive external contact surface 862. For some applications, distal-electrically-conductive external contact surface 862 faces at least partially radially outward. Optionally, distal-electrically-conductive external contact surface 862 additionally faces proximally and/or distally; for example, distal-electrically-conductive external contact surface 862 may include a radially-outward-facing portion 863, a proximally-facing portion 865, and/or a distally-facing portion 871. Optionally, proximally-facing portion 865 surrounds proximal-electrically-conductive external contact surface 860.

For some applications, such as shown, proximal-electrically-conductive external contact surface 860 does not reach a radially-outer-most surface of connector 832 (which, for example, may define distal-electrically-conductive external contact surface 862, such as shown). For other applications, proximal-electrically-conductive external contact surface 860 reaches the radially-outer-most surface of connector 832 (configuration not shown).

For some applications, such as shown in FIG. 20C, a drill shaft 830 of drill bit 820 comprises an electrically-conductive inner electrode 846, which has a proximal end portion 848 that is integral with proximal electrically-conductive coupler 836 of connector 832 of drill bit 820.

Figure 21A:
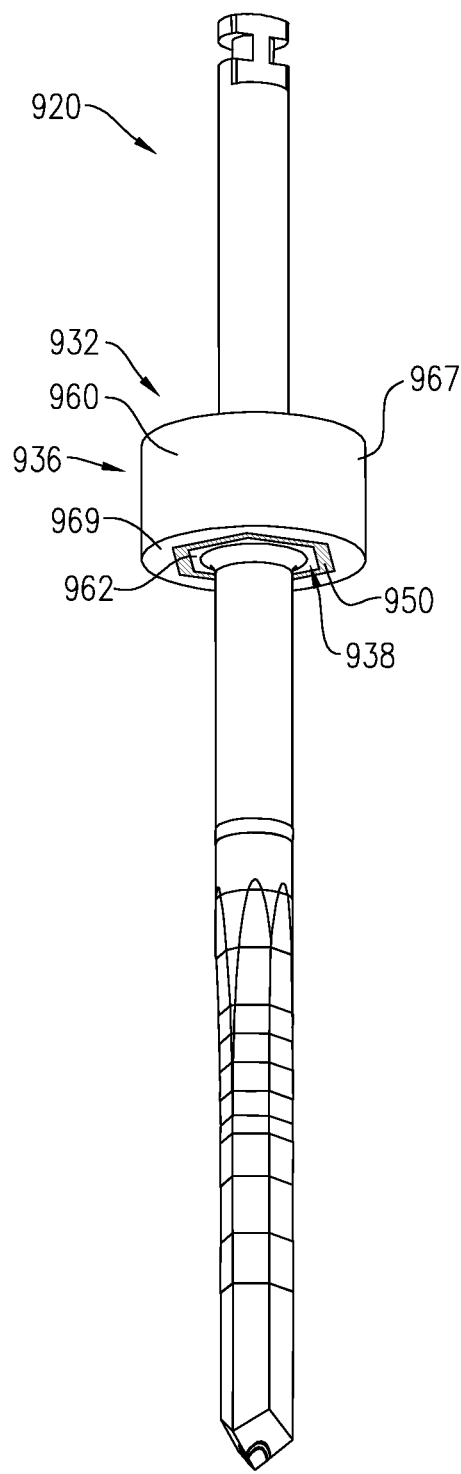
FIGS. 21A-B are schematic illustrations of yet another drill bit, in accordance with an application of the present invention.
Figure 21B:
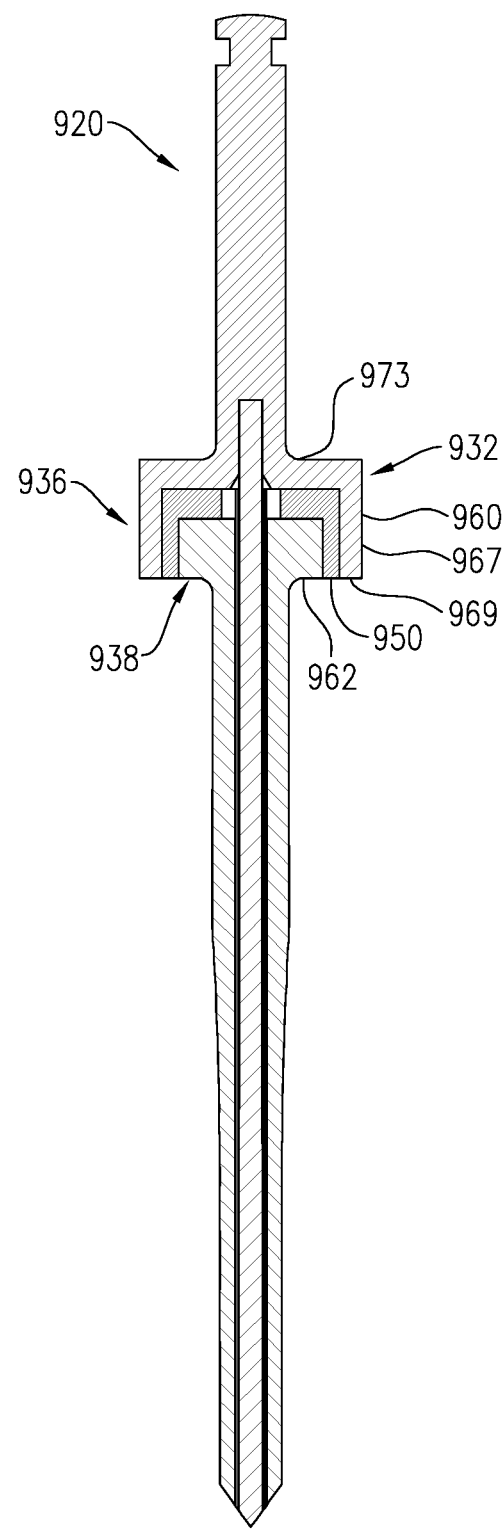

Reference is now made to FIGS. 21A-B, which are schematic illustrations of a drill bit 920, in accordance with an application of the present invention. Other than as described below, drill bit 920 is generally similar to drill bit 20, described hereinabove with reference to FIGS. 1A-4B, and may implement any of the features thereof, as well as any of the features of the other drill bits described herein, mutatis mutandis.

A connector 932 of drill bit 920 comprises a proximal electrically-conductive coupler 936 and a distal electrically-conductive coupler 938, which is shaped so as to define a distal-electrically-conductive external contact surface 962. Connector 932 further comprises an insulator 950 that electrically isolates distal electrically-conductive coupler 938 from proximal electrically-conductive coupler 936. Insulator 950 may implement any of the features of the other insulators described herein, mutatis mutandis.

Distal-electrically-conductive external contact surface 962 faces at least partially distally, such as entirely distally, as shown. For some of these applications, distal-electrically-conductive external contact surface 962 surrounds 360 degrees of a central longitudinal axis of connector 932.

Typically, proximal electrically-conductive coupler 936 is shaped so as to define a proximal-electrically-conductive external contact surface 960. For some applications, proximal-electrically-conductive external contact surface 960 faces at least partially radially outward. Optionally, proximal-electrically-conductive external contact surface 960 additionally faces proximally and/or distally; for example, proximal-electrically-conductive external contact surface 960 may include a radially-outward-facing portion 967, a distally-facing portion 969, and/or a proximally-facing portion 973. Optionally, distally-facing portion 969 surrounds distal-electrically-conductive external contact surface 962.

For some applications, such as shown, distal-electrically-conductive external contact surface 962 does not reach a radially-outer-most surface of connector 932 (which, for example, may define proximal-electrically-conductive external contact surface 960, such as shown). For other applications, distal-electrically-conductive external contact surface 962 reaches the radially-outer-most surface of connector 932 (configuration not shown).

Figure 22A:
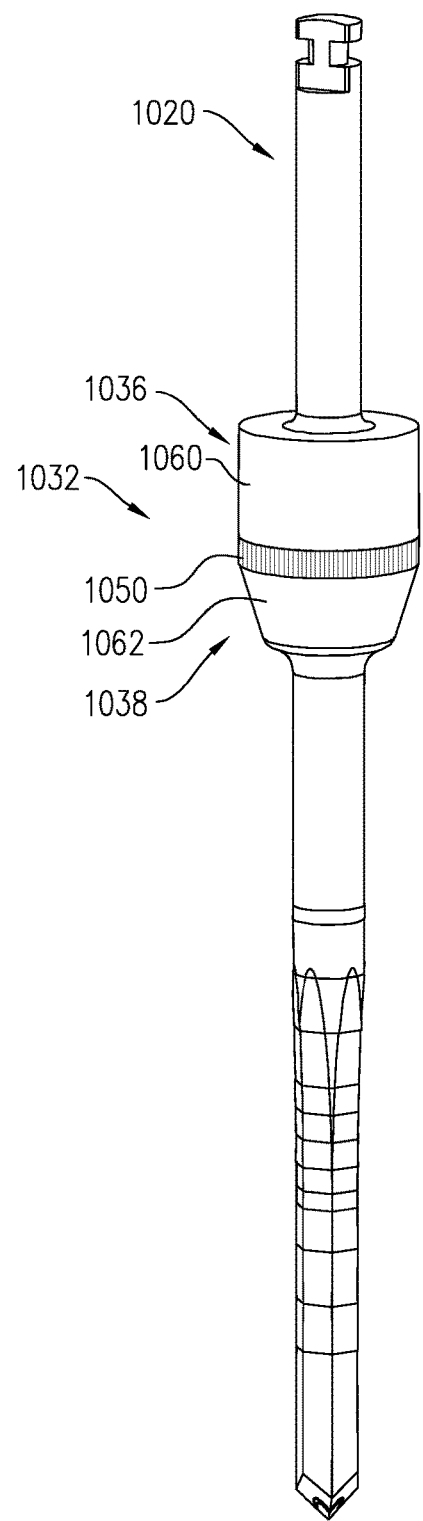
FIGS. 22A-B are schematic illustrations of still another drill bit, in accordance with an application of the present invention.
Figure 22B:
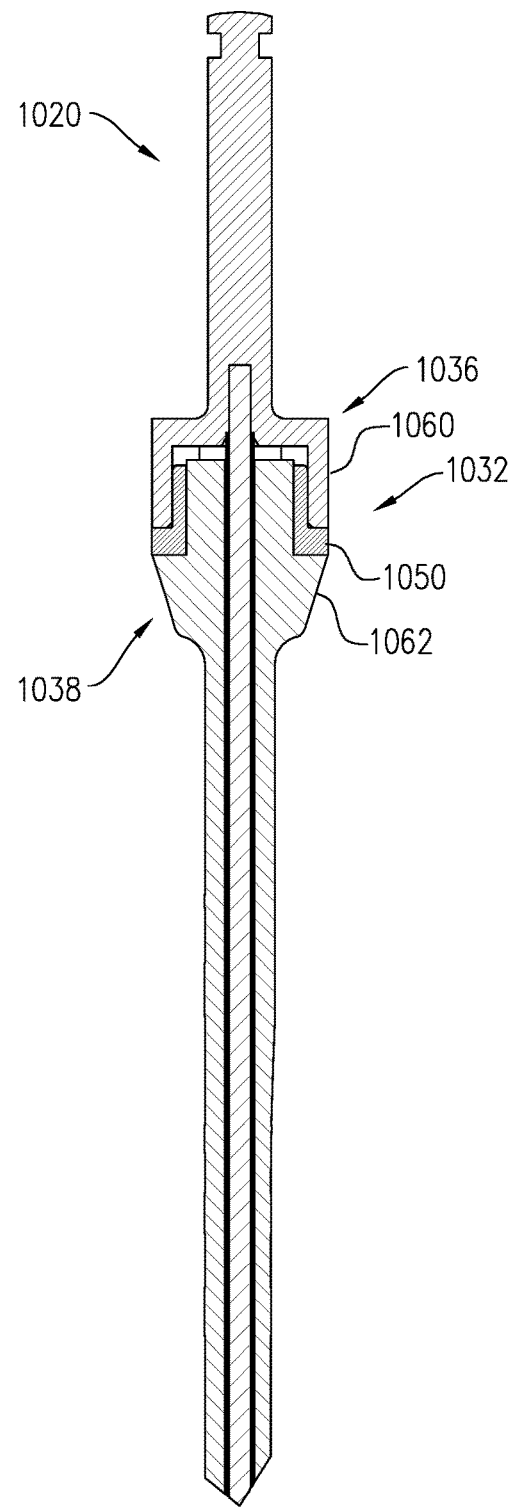

Reference is now made to FIGS. 22A-B, which are schematic illustrations of a drill bit 1020, in accordance with an application of the present invention. Other than as described below, drill bit 1020 is generally similar to drill bit 20, described hereinabove with reference to FIGS. 1A-4B, and may implement any of the features thereof, as well as any of the features of the other drill bits described herein, mutatis mutandis.

A connector 1032 of drill bit 1020 comprises a proximal electrically-conductive coupler 1036 and a distal electrically-conductive coupler 1038, which is shaped so as to define a distal-electrically-conductive external contact surface 1062. Connector 1032 further comprises an insulator 1050 that electrically isolates distal electrically-conductive coupler 1038 from proximal electrically-conductive coupler 1036. Insulator 1050 may implement any of the features of the other insulators described herein, mutatis mutandis.

Distal-electrically-conductive external contact surface 1062 faces partially distally, i.e., is oblique. A circular cross-section of distal-electrically-conductive external contact surface 1062 has a varying diameter along distal-electrically-conductive external contact surface 1062. For example, distal-electrically-conductive external contact surface 1062 may be conical and/or chamfered. Alternatively or additionally, for some applications, proximal-electrically-conductive external contact surface 1060 may be oblique, such as described regarding distal-electrically-conductive external contact surface 1062.

For some of these applications, distal-electrically-conductive external contact surface 1062 surrounds 360 degrees of a central longitudinal axis of connector 1032.

For some applications, proximal electrically-conductive coupler 1036 is shaped so as to define a proximal-electrically-conductive external contact surface 1060, which may have any of the features of the proximal-electrically-conductive external contact surfaces described herein.

In an embodiment, techniques and apparatus described in U.S. Provisional Application 62/942,520, filed Dec. 2, 2019, which is incorporated herein by reference, are combined with techniques and apparatus described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A drill bit comprising:
   (a) a connector, which comprises:
      (i) a shank, configured to receive torque;
      (ii) a proximal electrically-conductive coupler, which is disposed at a distal end of the shank, rotationally fixed with respect to the shank; and
      (iii) a distal electrically-conductive coupler, which is (1) rotationally fixed with respect to the proximal electrically-conductive coupler, (2) electrically isolated from the proximal electrically-conductive coupler, and (3) shaped so as to define a distal-electrically-conductive external contact surface; and
   (b) a drill shaft, which is shaped so as to define:
      (i) a proximal interface that is rotationally fixed with respect to the proximal electrically-conductive coupler and configured to transfer the torque from the proximal electrically-conductive coupler to the drill shaft, and
      (ii) a distal end portion that is shaped so as to penetrate tissue when rotated, wherein the drill shaft comprises:
         (i) an electrically-conductive outer electrode, which is in electrical communication with the distal electrically-conductive coupler;
         (ii) an electrically-conductive inner electrode, which has a proximal end portion that is in electrical communication with the proximal electrically-conductive coupler of the connector, and is electrically isolated from the distal electrically-conductive coupler of the connector; and
         (iii) an electrical isolation layer radially between the electrically-conductive outer electrode and the electrically-conductive inner electrode, so as to electrically isolate the electrically-conductive outer electrode and the electrically-conductive inner electrode from each other.

2. The drill bit according to claim 1, wherein the shank is shaped so as to define a non-cross-sectionally-circular proximal axial portion for receiving the torque.

3. The drill bit according to claim 1, wherein the shank is shaped so as to define a cross-sectionally-circular proximal axial portion for receiving the torque.

4. The drill bit according to claim 1, wherein the proximal interface of the drill shaft is rotationally fixed to the proximal electrically-conductive coupler via the distal electrically-conductive coupler.

5. The drill bit according to claim 1, wherein the distal electrically-conductive coupler is integral to the drill shaft at the proximal interface of the drill shaft.

6. The drill bit according to claim 1, wherein the distal electrically-conductive coupler and the drill shaft comprise separate pieces that are coupled together at the proximal interface of the drill shaft.

7. The drill bit according to claim 1, wherein the connector and the drill shaft comprise separate pieces that are removably couplable to each other.

8. The drill bit according to claim 1, wherein the proximal end portion of the electrically-conductive inner electrode and the proximal electrically-conductive coupler of the connector comprise separate pieces that are directly coupled to each other.

9. The drill bit according to claim 1, wherein the proximal end portion of the electrically-conductive inner electrode is integral with the proximal electrically-conductive coupler of the connector.

10. The drill bit according to claim 1,
wherein the connector further comprises an internal electrical contact, which is in electrical contact with the proximal electrically-conductive coupler and is electrically isolated from the distal electrically-conductive coupler, and
wherein the proximal end portion of the electrically-conductive inner electrode is in electrical communication with the proximal electrically-conductive coupler via the internal electrical contact.

11. The drill bit according to claim 10, wherein the internal electrical contact comprises a contact spring.

12. The drill bit according to claim 11, wherein the contact spring is in axial contact with the proximal end portion of the electrically-conductive inner electrode.

13. The drill bit according to claim 11, wherein the contact spring is in lateral contact with the proximal end portion of the electrically-conductive inner electrode.

14. The drill bit according to claim 1, wherein the electrically- conductive inner electrode protrudes proximally from the distal electrically-conductive coupler of the connector.

15. The drill bit according to claim 1, wherein the electrically-conductive inner electrode is recessed within the distal electrically-conductive coupler of the connector.

16. The drill bit according to claim 1, wherein the electrically-conductive inner electrode is flush with the distal electrically-conductive coupler of the connector.

17. The drill bit according to claim 1, wherein a length of the shank, measured between a proximal end of the shank and the distal end of the shank, is between 5 and 30 mm.

18. The drill bit according to claim 1, wherein a length of the drill shaft, measured between the proximal interface of the drill shaft and a distal tip of the drill shaft, is between 3 and 80 mm.

19. The drill bit according to claim 1, wherein the electrically-conductive inner electrode is flush with a proximal end of the drill shaft.

* * * * *